(12) United States Patent
Albahri

(10) Patent No.: US 7,780,992 B2
(45) Date of Patent: Aug. 24, 2010

(54) ANTIVIRAL MEDICAMENT

(76) Inventor: Tareq Abduljalil Albahri, 32 37$^{th}$ street Block 7, Jaber Al-Ali (KW) 51607

( * ) Notice: Subject to any disclaimer, the term of this patent is extended or adjusted under 35 U.S.C. 154(b) by 1437 days.

(21) Appl. No.: 10/315,446

(22) Filed: Dec. 8, 2002

(65) Prior Publication Data

US 2004/0109899 A1    Jun. 10, 2004

(51) Int. Cl.
*A61K 35/23* (2006.01)

(52) U.S. Cl. ...................... 424/558; 424/520

(58) Field of Classification Search .............. None
See application file for complete search history.

(56) References Cited

U.S. PATENT DOCUMENTS

| | | | |
|---|---|---|---|
| 3,282,788 A * | 11/1966 | Daniels et al. ............ | 424/558 |
| 4,315,916 A | 2/1982 | Likens et al. | |
| 4,595,591 A | 6/1986 | Mardi et al. | |
| 4,774,229 A | 9/1988 | Jordan | |
| 4,822,607 A | 4/1989 | Balassa et al. | |
| 4,891,227 A | 1/1990 | Thaman et al. | |
| 5,073,630 A | 12/1991 | Nunes et al. | |
| 5,492,935 A | 2/1996 | Yu et al. | |
| 5,500,359 A | 3/1996 | Boyer et al. | |
| 5,532,215 A | 7/1996 | Lezdey et al. | |
| 5,662,903 A | 9/1997 | Boyer et al. | |
| 5,705,518 A | 1/1998 | Richter et al. | |
| 5,997,549 A | 12/1999 | Sauceda et al. | |
| 6,028,118 A | 2/2000 | Dupont et al. | |
| 6,063,381 A | 5/2000 | Staggs | |
| 6,132,756 A | 10/2000 | Haque et al. | |
| 6,165,481 A | 12/2000 | Kaiya et al. | |
| 6,197,808 B1 | 3/2001 | Cheng et al. | |
| 6,306,383 B1 | 10/2001 | Crandall | |
| 6,306,397 B1 | 10/2001 | Edwards et al. | |
| 6,309,662 B1 | 10/2001 | Buchanan | |
| 6,312,735 B1 | 11/2001 | Niazi et al. | |
| 6,335,023 B1 | 1/2002 | Yu et al. | |
| 6,350,451 B1 | 2/2002 | Horn et al. | |
| 6,372,218 B1 | 4/2002 | Cummins | |
| 2001/0051184 A1 | 12/2001 | Heng | |

FOREIGN PATENT DOCUMENTS

| | | |
|---|---|---|
| EP | 0842660 A1 | 5/1998 |
| WO | WO-9964029 A1 | 12/1999 |

OTHER PUBLICATIONS

Miller (recipe for Stir-Fried Pork Kidney and Snow Peas, pp. 159-160, The Thousand Recipe Chinese Cookbook, copyright 1994, Simon & Schuster, Inc.).*
Rogov (Rogov's Ramblings, website of recipes updated Jun. 15, 2001, available from www.stratsplace.com/rogov/pot_pourri.html, 26 page print-out).*

* cited by examiner

*Primary Examiner*—Stacy B Chen
(74) *Attorney, Agent, or Firm*—Lowe Hauptman Ham & Berner, LLP

(57) ABSTRACT

There is disclosed a prophylactic and therapeutic antiviral composition and in particular compositions which comprise containing vertebrates kidney as a main component. Use of the composition through parenteral administration for the prevention and treatment of viral-induced tumors, lesions and diseases in mammals such as humans or to prepare a medicament is also disclosed. The composition is very effective in preventing and treating viral infections and manifestations as hyperplasia, keratosis, and dermatosis and in particular those caused by Papillomavirus and more particularly Human Papillomavirus. Among the many benefits, the present compounds provide high remedial effect and complete resolution in a relatively short course of treatment with no risk of side effects what so ever. The composition is abundant, inexpensive, easily prepared, and may be self administered to the afflicted area by the patients themselves.

6 Claims, No Drawings

ANTIVIRAL MEDICAMENT

BACKGROUND OF THE INVENTION

1. Field of the Invention

The present invention provides compositions and methods for modulating cutaneous and mucocutaneous or mucosal proliferations that are benign or malignant, which are of viral origin such as common warts and plane warts. The methods and compositions disclosed herein provide for the treatment and prevention of a variety of damaged epithelial and mucosal tissues, particularly those resulting from hyperplastic or neoplastic conditions, especially those having a papillomavirus as a causative agent. For instance, it will be evident that the method will find ready application for the therapy or prophylaxis of, for example, verrucous lesions such as verruca plana, verruca acuminata, and other verruciform lesions marked by proliferation of epithelial cells. The subject compositions can also be used in the treatment of other epithelial proliferative or systemic disorders caused by wart viruses. For example, bowenoid papulosus is a tumor of the genitalia induced by premalignant wart viruses and usually afflicting men. Condylomatous dysplasia and cervical carcinoma in situ are premalignant tumors of the female genitalia, also induced by wart viruses. Known treatments for all these tumors are painful and not always effective. According to the present invention, such therapies can be augmented or replaced by treatment with the subject preparations.

2. Introduction

Dermatosis is generally used to describe any disease of the skin. Keratosis and Hyperplasia are generally used to describe those characterized by an overgrowth of the epithelium. In particular, these diseases include what are commonly referred to as warts, corns and calluses.

A wart (also known as verrucas) is a small flesh-colored usually hard tumorous growth of the skin which is characterized by circumscribed hypertrophy of the papillae of the corium, with thickening of the malpighian, granulation and keratin layers of the epidermis. Verucca vulgaris, a subset of warts or verruca, is characterized by infection of the keratinocytes with human papillomavirus.

Warts are a very common superficial lesions and tumors of the skin of benign, premalignant and malignant type. They are defined as a small intra-epidermal papillomatous growth which occurs on the surface of the skin of an animal body, with generally warts being common within humans of all ages. Papillomas (warts) have been detected based upon their histological characteristics at numerous sites in humans on the skin and the mucous membranes including the hands, face, feet, larynx, genitalia, genital tract, respiratory tract, and oral cavity.

Warts are caused by various human papillomaviruses through direct contact with the virulent particle. Warts are infectious and can be autoinoculated and spread to other individuals by direct contact. Each papillomavirus is related to a specific clinical presentation of the wart as shown in Table 1. Representative examples of wart conditions include benign cutaneous warts and in particular common warts (verruca plana) and plantar warts (verruca plantaris), Butcher's common warts, epidermodysplasia verruciformis (EV), flat (non-condylomatous) warts, plane or intermediary skin warts, genital (such as penile, anal, labial, and cervical) warts, seborrhoic warts (verruca senilis), juvenile warts (verruca plana), verruca vulgaris, intra-epithelial neoplasias and papillomas.

Verrucae warts are lumpy typically flesh colored and have rough surface. Finger-like projections and sometimes dark specks are present, which are the result of thrombosed capillaries. Usually these warts are found on the face and scalp. Plantar warts are found on the planter surface of the feet and can be deep and painful. These warts occur singularly, in clusters or spread over a wide area. Flat warts are typically small, flat-topped, flesh colored papules that occur primarily on the face, hands and forearms. Usually the surface of the wart is smooth and they may appear in the hundreds. Genital warts are soft, flesh colored or slightly pigmented and occur in the genitalia of the mammal and are sexually transmitted. Chronic infections of the viruses that cause genital warts in women are a serious problem as intra epithelial neoplasia or squamous cell carcinoma may develop.

HPV infection is a systemic rather than just a localized skin manifestation. The risk of infection of warts depend not only the virulence of the virus particles, but also on the patient's susceptibility to viral attack and strength of the patient's immune system. Immunodeficient patients have greater susceptibility to infection, inadequate treatment for HPV, and frequent recurrences. States of immunocompromization created by conditions such as pregnancy, organ transplants, chemotherapy, stress, old age, infancy, illness, or infections are risk factors for wart recurrence. All patients with HPV will be vulnerable to recurrences for the rest of their lives. Recently, it has also been observed that individuals with depressed immune systems, such as sufferers of Acquired Immune Deficiency Syndrome (AIDS), are prone to (HPV) infections which can result in tumor growth over their entire bodies, resulting in great mental and physical distress to the afflicted individual.

Host immune responses to papillomavirus infection are not well understood but infection usually occurs in the young, followed by persistence of the wart for a variable period of time. After spontaneous regression, if at all, the host is left immune to reinfection by the same virus. In humans, antibody response to HPV infection is characterized by the appearance of IgM antibodies prior to the onset of regression. Just subsequent to regression, both IgM and IgG antibodies are present; long after regression, only IgG is detectable. This conversion from IgM to IgG has been observed in cattle experimentally infected with Bovin Papillomavirus (BPV) as well.

In humans, regressing flat warts demonstrate a similar histological appearance with perivascular infiltration of mononuclear leukocytes in the upper dermis, with epidermal invasion sharply confined to the papilloma. This simultaneous regression of multiple warts at distant sites suggests that cell-mediated immunity plays a major role in papilloma rejection. Regression of flat warts, however, has no effect on plantar or palmar warts in the same individual, indicating that regression is HPV type-specific. A similar differential regression of warts has also been observed in cattle infected with multiple BPV types.

Untreated or recurrent anogenital warts can be transmitted not only sexually, but from infected mother to her child. HPV has been found in the amniotic fluid from some pregnant women with cervical lesions. This very early transmission source as well as the presence of warts in the birth canal can lead to the development of life-threatening laryngeal papillomas. These may not develop at birth but can develop anytime during the first few years of a child's life, the median age being 3 years of age. There are also cases of newborns with anotenital warts present at birth or developing them in the first few years after birth. Autoinoculation and fomite transmission are other vehicles of non-sexual transmission of the genital human papillomavirus infection. Active genital warts can be identified in approximately 2.5% of pregnant American women, thus being implicated in 60,000 to 90,000 pregnancies annually. HPV infections are more than twice as prevalent in pregnant women. Each year there are an estimated 1,500 new cases of laryngeal papillomatosis, indicating that the risk of infection from mother to newborn ranges from 1:80 to 1:200.

Papillomaviruses (PVs) are members of the papovavirus (PPV) family. PVs are a heterogeneous group of closely related small (50-60 nm) nonenveloped double-stranded covalently closed icosahedral DNA molecules. Papillomaviruses replicate in the nucleus of squamous epithelial cells and cannot be multiplied by culture. Although differing very much from each other, PV's have molecular sizes of the order to 7,000-8,000 base pairs and their genomes do nonetheless exhibit certain degrees of homology.

Papillomaviruses may be classified into distinct groups based on the host that they infect. The complete nucleotide sequence and genetic organization of a number of animal and human PV's have been determined including the human papillomavirus (HPV), cottontail rabbit papillomavirus (CRPV), equine papillomavirus (EPV) and Bovine papillomavirus (BPV).

Papillomaviruses are spread widely throughout nature and can produce a spectrum of diseases in a variety of higher vertebrates. They have been detected and isolated from humans, cattle, sheep, dogs, cats, rabbits, monkeys, snakes, horses, cows, deer and several avian species.

Papillomaviruses are remarkably species specific infective agents; a human papillomavirus cannot infect a nonhuman animal. Because the genomic organization is highly conserved among papillomaviruses, it is reasonable to assume similar relationships with respect to genome structure and function between animal and human papillomaviruses. Since some of the animal papillomaviruses are highly oncogenic, it is likely that all or a portion of this function may be a property of some of the HPVs as well.

Papillomaviruses (PVs) infect epithelial cells and are causative of proliferative lesions at the site of infection particularly, benign epithelial or fibroepithelial tumors (fibropapillomas), commonly known as warts. Although these viruses are generally associated with benign lesions, a specific subset of the viruses has been associated with hyperplasias capable of degenerating into intra-epithelial neoplasias and cutaneous carcinomas. The implication that these viruses may play an etiologic role in the development of some human cancers follows from numerous studies that have shown the presence of transcriptionally active human papillomavirus (HPV) deoxyribonucleic acids in a high percentage of certain cancerous lesions. Although papillomaviruses (PVs) are implicated in the etiology of cancers, the complete story of their involvement is not yet known.

Among papillomavirus infections mention should also be mad more particularly of benign dysplastic hyperproliferations of skin and mucosal epithelium such as cutaneous warts and in particular common warts and plantar warts, epidermodysplasia verruciformis (EV), plane or intermediary skin warts, and intra-epithelial neoplasias. The Papillomavirus (PV) have also been linked to widespread, serious human diseases, malignant and premalignant hyperproliferations of skin and mucosal epithelium especially; the cancers of the epidermodysplasia verruciformis (EV), oral, respiratory or laryngeal papillomatosis, focal epithelial hyperplasia, genital neoplasias and cancers of the uterine cervix (cervical carcinoma), condyloma acuminatum, cutaneous cancers, condylomas and papillomas. In addition, papillomavirus has been implicated as a causative agent in nasal tumors, and various oral cancers.

Although PVs are epitheliotropic, they also show remarkable tissue specificity and strong cellular tropism. For example, HPVs have a tropism for squamous epithelial cells and infect only surface epithelia of cutaneous and mucous membranes.

The human papillomavirus (HPV) was initially discovered in connection with benign hyperplastic (common warts and condylomata in the genital region) and pre-malignant and malignant lesions (carcinomas of the skin and vagina) of squamous epithelial neoplasms. Considerable insight into HPV biology and their involvement in human disease has been attained by the application of the techniques of molecular biology.

Infection with HPV may result in cutaneous neoplasia including common warts of the hands and feet, laryngeal warts and genital warts which may develop into genital, cervical or laryngeal carcinoma, and may be associated with as many as 90% of the condylomas and cervical carcinomas. The human papillomavirus (HPV) is also a major cause of vulvovaginal infection. The lesions from HPV are usually not described as vulvovaginitis although they do cause vulvovaginal infection. The condition is not inflammatory (vaginitis) but rather wart-like outgrowths of the tissue of the vagina, vulva and cervix and usually do not elicit any symptoms of pain or itching. But most importantly HPV is probably the most significant cause of cervical cancer in women.

Formation of an HPV-induced tumor is thought to require infection of an epithelial basal cell and the expression of viral early proteins in order to stimulate cell proliferation. The late stages of the virus life cycle, which ultimately lead to the production of infectious virions, are initiated only as the infected cell migrates through the upper differentiated layers of the epidermis.

The clinical importance of warts varies considerably and determinative factors are the infecting viral type, the location of the wart, and factors unique to the host. For example, a wart located on the skin is often clinically insignificant, being self limiting. However, warts on the vocal cords may be life threatening as a result of respiratory obstruction. Skin warts may spontaneously regress within a few years after their initial appearance but may also persist for decades. The exception is a rare life threatening papillomavirus disease termed epidermodyspasia verruciformis (EV). In this disease, the infected individual does not experience spontaneous regression, but rather the infection may progress to a malignant stage. The disease is present world-wide, but is rare and is often found among family members. Thus, genetic factors are thought to be involved in the etiology of the disease.

Warts are not just insignificant lesions, but can in the future lead to malignancies regardless of the immune status of the patient or HPV type. A possible role for HPVs in human cancer was suspected following the detection of HPV DNA genomes in tumors resulting from the malignant conversion of genital warts. Some of these HPVs have been strongly implicated as etiologic agents in dysplasia and carcinomas in the oral and genital mucosa of the infected mammal. Low risk types of HPV do not necessarily mean no risk for malignancies. High risk types of HPV and immunodeficiencies only create a greater predisposition leading to the process of malignant transformation. This phenomenon of malignant transformation is frequently seen in immunocompromised patients and in viral persistence of high risk HPV types.

Two types of precancerous changes have been characterized: the first is dysplasia, which is an impairment of the normal progress of cervical basal cells toward terminal differentiation into squamous epithelia. The second is condyloma, a wart-like precanerous change known to be of viral origin. Both dysplasia and condyloma may be induced by human papilloma viruses.

Genital warts, also referred to as venereal warts and condylomata acuminata, are one of the most serious manifestations of PV infection. As reported by the Center for Disease Control, the sexual mode of transmission of genital warts is well established and the incidence of genital warts is on the increase. Data collected from the National Therapeutic Index showed that in 1984 there were 224,900 first office visits for genital warts and 156,720 first office visits for genital herpes in the US. The incidence of genital warts has steadily increased throughout the 1970s and 1980s, as was recently demonstrated by an epidemiological study in which the mean incidence from 1950 to 1978 reached a peak of 1.065 per 1,000 populations. The prevalence of cervical HPV infection in women aged 25 to 55 proved to be 0.8%, but in 22 year old women it was 2.7%. Recent studies on cytologically normal women have demonstrated the incidence of latent infection to be 11%. Thus, there appears to be a latent stage of the disease which suggests an even greater incidence and prevalence.

The seriousness of genital warts is underlined by the recent discovery that HPV DNA can be found in all grades of cervical intraepithelial neoplasia (CIN I-III) and that a specific subset of HPV types can be found in carcinoma in situ of the cervix. Consequently, women with genital warts, containing specific HPV types are now considered at high risk for the development of cervical cancer. Currently, tens of millions of women worldwide suffer from human papilloma virus (HPV) infection of the genital tract. There is reported to be well over a million cases in the United States alone. Significant number of these women eventually develop cervical cancer of which there are about 500,000 new cases diagnosed yearly worldwide. As many as 90% of all cervical cancer maybe linked to HPV. It has been estimated that perhaps twenty percent (20%) of all cancer deaths in women worldwide are from cancers which are associated with HPV.

Whereas penile warts in males only very rarely result in cancer of the penis, when transmitted to the cervix cancer is much more likely to follow. About one-third of patients who have histologically-confirmed HPV infection of the cervix can be expected to develop cervical intraepithelial neoplasia (CIN) within a year. The lag time between infection and cancer is, however, often 10-30 years.

Condyloma acuminata is a tumor (wart) detectable on the skin or mucous membrane of the genital organs of the mammals such as men and women, and is caused by human papilloma virus (HPV). The site of infection in men is the balanic area, coronary sulcus, foreskin, anal area, urethral meatus, and in women is the vagina, labium, anal area and urethral orifice. Clinical symptoms appear from 1-6 months, on average 3 months after infection, but usually symptoms are not noticed by the patient. This wart shows distinctive papillary or cockscomb-like tumors and has a tendency to accumulate and multiply and is usually red or reddish brown in color. Genital warts are soft, flesh colored or slightly pigmented and are sexually transmitted. Chronic infections of the viruses that cause genital warts in women are a serious problem as they may develop into genital carcinoma.

Human papillomaviruses (HPVs) comprise a group of at least 75 types, based on DNA sequence homology as measured by liquid hybridization. A certain number of types of papillomavirus have already been described. Mention should be made of new types and subtypes of papillomaviruses which have been isolated from warts or disseminated macular lesions, among which some are more likely than others to give rise to the early development of cancers of the skin in patients who are infected by them. The definition of a new type is that it possesses less than 50% cross hybridisation with the DNA of known species in the liquid phase according to a standard protocol. The present invention relates to several types and subtypes of these new papillomaviruses taken individually or in combination among themselves and/or with the DNAs of previously known HPVs.

Papillomaviruses (PVs) cause epithelial tumors in humans which vary in severity depending on the site of infection and the human papilloma virus (HPV) type involved. Each HPV type exhibits host specificity, has a preferred anatomical site of infection, and can generally be associated with a specific lesion or disease. For example, HPV 1 causes benign skin tumours, verruca vulgaris or common wart, and plantar warts, whereas HPV 7 causes common and butchers' warts. Viruses infecting cutaneous surfaces are more likely to have some degree of homology to other HPVs infecting the skin than those infecting mucosal surfaces. Cutaneous infections include among others plantar wart, common wart, Butchers' common wart, flat wart, and epidermodysplasia verruciformis (EV), whereas, mucocutaneous or mucosal infections include genital wart, condyloma acuminatum, laryngeal papilloma, focal epithelial hyperplasia, and cervical carcinoma.

Further, although a particular virus type is preferentially associated with a given lesion, it may, on occasion, be found in other lesions. HPV-1 for example is associated with about 85% of plantar warts but HPV-2 has also been detected in a small percentage of plantar warts and vice versa. HPVs may be grouped with respect to sequence homology and site of infection. A non-limiting list of additional retroviruses included within the scope of the present invention is set out in Table 1.

In humans, different papillomavirus types are known to cause distinct diseases and appear at different sites in the body. For example, HPV types 1, 2, 3, 4, 7, 10 and 26-29 cause benign warts in both normal and immunocompromised individuals. HPV types 5, 8, 9, 12, 14, 15, 17, 19-25, 36 and 46-50 cause flat lesions in immunocompromised individuals. HPV types 6b, 11a, 13 and 16 are associated with lesions to mucous membranes. Cutaneous lesions, such as those induced by HPV types 5, 8, 14, 17, 20, are difficult to manage clinically, and are often associated with malignancies in immunosuppressed patients. HPV types 6, 11, 34, 39, 41-44 and 51-55 cause nonmalignant condylomata of the genital, anal, cervical or respiratory mucosa. These infections have a low risk of progression to cancer but are difficult to eradicate and are disruptive to the lives of the patients. The higher risk mucosal types 16, 18, 31, 33, 35, 39, 45, 51, 52, 55, 56, 58, and 61 cause on the other hand mainly asymptomatic flat, almost invisible lesions (flat condyloma) which can progress to high grade cervical intraepithelial neoplasia (CIN). These CIN-lesions can develop further to cervix cancer even if comparatively seldom. The highest risk of progression to malignancy is associated with lesions caused by HPV types 16, 18, 45 and 56.

HPV types 16, 18, 31 and 33 are particularly common in cervical cancers; HPV types 16 and 18 cause epithelial dysplasia of the genital mucosa and are associated with the majority of in situ and invasive malignant squamous cell carcinoma from cancer of the cervix, vagina, vulva, penis, anal canal, and Condyloma acuminata. More than 90% of all cervix cancers carry some type of HPV. HPV 16 alone is found in about 60% of all cervical tumours and about 50% of all cervical cancers indicating strong relation to the malignancy of Condyloma acuminata. These HPVs are referred to as "high risk" HPVs. HPV6 and HPV11 are two closely related viruses and most commonly detected. They are causative agents for

TABLE 1

HPV-DNA DIAGNOSIS OF PAPILLOMA VIRUS INFECTIONS.

| | HPV type | HPV Disease |
|---|---|---|
| 1 | 1, 2d, 4 | Common warts and mucosal warts (verrucae and plantar). |
| 2 | 2, 26, 63 | Common warts. |
| 3 | 3 | Common, mucosal, intermediary, flat, and plane warts, intra-epithelial neoplasias, cutaneous cancers, and EV. |
| 4 | 3a, 14a, 17b | Epidermodysplasia verruciformis (EV). |
| 5 | 5, 8 | Flat warts, squamous cell carcinoma (SCC), intra-epithelial neoplasias, cutaneous cancers, EV and EV cancers. |
| 6 | 6 | Laryngeal papillomas and genital warts (condyloma) |
| 7 | 6b | Mucosal warts and genital warts (condyloma). |
| 8 | 7 | Common warts, Butchers' common warts. |
| 9 | 9, 15, 17, 19, 20, 21, 22, 23 | Flat warts and epidermodysplasia verruciformis (EV). |
| 10 | 10 | Flat warts, common warts, and EV. |
| 11 | 10a, 10b | Mucosal warts, common warts, intermediary warts, plane warts, intra-epithelial neoplasias, cutaneous cancers, and EV. |
| 12 | 11 | Laryngeal papillomas, Condyloma (Genital warts), Condyloma acuminata. |
| 13 | 11a | Mucosal warts. |
| 14 | 12 | Flat warts, Intra-epithelial neoplasias and cutaneous cancers, EV and EV cancers. |
| 15 | 13 | Mucosal warts, focal epithelial hyperplasia, and oral epitehlial hyperplasia (oral intraepithelial neoplasias). |
| 16 | 14, 25, 36, 46, 47, 48 | Flat warts |
| 17 | 14b | Intra-epithelial neoplasias, EV, and EV cutaneous cancers. |
| 18 | 16 | Flat warts, anal warts, mucosal warts, condyloma (genital warts), condyloma acuminate, CIN, and cervical carcinoma, |
| 19 | 17a | Intra-epithelial neoplasias, EV, and cutaneous cancers. |
| 20 | 18 | CIN, genital and cervical carcinoma. |
| 21 | 24, 50 | Flat warts, EV, intra-epithelial neoplasias and cutaneous cancers |
| 22 | 27 | Common warts and cervical intraepithelial neoplasia (CIN) |
| 23 | 28, 29 | Common, mucosal, intermediary, and plane warts, intra-epithelial neoplasias, and cutaneous cancers. |
| 24 | 31 | Flat warts, cervical carcinoma, cervical intraepithelial neoplasia (CIN), oral epitehlial hyperplasia (oral intraepithelial neoplasias). |
| 25 | 32 | Intra-epithelial neoplasias and cutaneous cancers. |
| 26 | 33, 35, 45, 56, 58, 61 | Cervical intraepithelial neoplasia (CIN) and cervical carcinoma. |
| 27 | 34, 41, 42, 43, 44, 53, 54 | Genital warts and laryngeal papillomas. |
| 28 | 39, 51, 52 | Genital warts, CIN, cervical carcinoma and laryngeal papillomas. |
| 29 | 49 | Common, flat, and plantar warts. |
| 30 | 55 | Laryngeal papillomas, genital neoplasias and cancers of the uterine cervix, condylomas and papillomas, Genital warts, CIN. | more than 90% of all condyloma (pointed genital warts) and laryngeal papillomas. These infections rarely progress to invasive cancer, and therefore these HPVs are referred to as "low risk" HPVs. In some rare cases, however, HPV6 and 11 can also be associated with CIN and cervix cancer. The most abundant subtype of HPV type 6 is HPV6a. Furthermore, HPV49 causes warts of the skin (in particular, common and plantar warts) and the differential diagnosis of epidermodysplasia verruciformis (EV). HPV50 causes epidermodysplasia verruciformis (EV), intra-epithelial neoplasias and cutaneous cancers. HPV55 causes genital neoplasias and cancers of the uterine cervix, condylomas and papillomas.

The most common disease associated with papillomavirus infection is benign skin warts. Common warts (also known as benign cutaneous warts) generally contain HPV types 1, 2, 3, 4 or 10. These warts typically occur on the soles of feet, plantar warts, or on the hands. Common skin warts are most often found in children and young adults. Later in life the incidence of common warts decreases presumably due to immunologic and physiologic changes. Plantar warts can often be debilitating and require surgical removal and they frequently reoccur after surgery. To date there is no reliable treatment for plantar warts. Common warts of the hands are unsightly but rarely become debilitating and are therefore not usually surgically treated.

Genital warts are the most frequently diagnosed, viral, sexually transmitted disease. Clinically, they may be categorized into two major groups: condyloma acuminata and flat cervical warts. Condylomas have been shown to contain virus particles and molecular studies have demonstrated that greater than 90% of these lesions contain either HPV-6 or HPV-11 DNA. Condyloma acuminata generally occur on the penis, vulva or in the perianal region. They may spontaneously regress or persist for years and progression to an invasive carcinoma occurs only at a low frequency. Unlike other genital warts, those occurring on the uterine cervix usually exhibit a flat rather than acuminate morphology, and are usually clinically detected by Pap smear. A papillomavirus etiology for cervical dysplasia was suggested by the studies of cytologists in the late 1970s who demonstrated the association on Pap smear of cytologic changes due to HPV infection with those of dysplasia. Other studies showed the presence of viral particles and viral capsid antigen in some of the dysplastic cells of these lesions. This association was important because previous clinical studies had established that cervical dysplasia (also referred to as cervical intra-epithelial neoplasia or CIN) was a precursor to carcinoma in situ which was in turn recognized to be a precursor to invasive squamous epithelial cell carcinoma (SCC) of the cervix.

A possible role for HPVs in human cancer was suspected following the detection of HPV DNA in tumors resulting from the malignant conversion of genital warts (cervical carcinoma). The cloning of two HPV genomes, HPV-16 and HPV-18 from cervical carcinomas has further stimulated research in this field of immense socio-economic importance. These were subsequently used as hybridization probes to show that more than 70% of the human cervical carcinomas and the derived cell lines scored positive for the presence of either of these HPV types. Another 20% contain additional HPV-types such as HPV-31, HPV-33, and HPV-35. Amongst these is HPV-33 which was recently cloned from an invasive cervical carcinoma using HPV-16 as a probe under conditions of reduced stringency.

Many HPV-induced lesions such as common warts, plantar warts, and flat warts are entirely benign and not clinically associated with progression to carcinomas. However, several HPVs are occasionally associated with subsequent development into squamous cell carcinomas, and HPV-5 has been associated with cutaneous carcinomas in patients with epidermodysplasia verruciformis (EV). Juvenile laryngeal papillomatosis is caused by papillomavirus HPV-11. Rare cases of spontaneous progression to invasive squamosal carcinoma of the larynx in the absence of irradiation have been described. More frequently following radiation therapy, progression of juvenile laryngeal papillomatosis progresses to squamous cell carcinoma (SCC).

Laryngeal papillomas are benign epithelial tumors of the larynx. Two HPV types, HPV-6 and HPV-11, are most commonly associated with laryngeal papillomas. Clinically, laryngeal papillomas are divided into two groups, juvenile onset and adult onset. In juvenile onset it is thought that the neonate is infected at the time of passage through the birth canal of a mother with a genital PV infection. Disease is usually manifest by age 2 and is characterized by the slow but steady growth of benign papillomas that will ultimately occlude the airway without surgical intervention. These children will typically undergo multiple surgeries with the papillomas always reoccurring. Patients will ultimately succumb to complications of multiple surgeries. To date there is no curative treatment for juvenile onset laryngeal papillomatosis and spontaneous regression is rare. Adult onset laryngeal papillomatosis is not as aggressive and will frequently undergo spontaneous remission.

Among HPV infections is epidermodysplasia verruciformis (EV). EV is a rare genetically transmitted recessive disorder which is characterized by generalized pityriasis-like lesions or disseminated flat warts that appear as small reddish macules. A variety of HPV types 3, 5, 8-10, 12-15, and 17 have been associated with EV. HPV3a and 10 which are associated with plane warts observed in some patients suffering from EV and in the population generally. DNA sequences similar to those of HPV3a have been found in a cancer of a patient suffering from EV. The genomes of HPV5 and 8 have been detected in cancers of patients suffering from EV. With the exception of types 3 and 10, this group of HPVs has not been detected in warts from healthy individuals, having only been identified in lesions from immunosuppressed renal allograft recipients. With time approximately one third of EV patients develop squamous cell carcinoma (SCC) of the skin at multiple sites. In general, SCC occurs on sun exposed areas of the skin. Only a subset of EV associated PV is consistently found in SCC. It has been reported that lesions containing HPV-5 and HPV-8 frequently undergo malignant conversion to SCC when present on sun-exposed areas. Genetic predisposition, immunologic abnormalities, and UV irradiation as well as HPV may all contribute to the development of SCC in these patients.

A number of types of papillomavirus have already been described. The framework of the present patent application includes many new types and subtypes of papillomavirus described herein and those that have not yet been discovered. The present patent also relates to mixtures or "cocktails" of DNA-HPVs isolated from the papillomaviruses which were new at that time and/or from papillomaviruses already known at the filing dates of the corresponding titles.

PRIOR ART REFERENCE AND DISCUSSION

In the past, there have been numerous lotions that have been designed to be appliable to the wart and, after a period of time, the wart is to drop off of the body. However, in the past, these lotions have proved to be rather ineffective and/or painful. In the 19th century, various metallic salts have been proposed for removing warts and other skin defects, among others copper salts like the acetate and the sulfate, lead salts in combination with zinc sulfate, copper sulfate and white vinegar, furthermore antimony, arsenic, chromium, mercury and silver salts as well as cadmium salts. Among all these salts, only zinc chloride when used together with trichloroacetic acid has reached some short-lived importance for treating skin cancer.

Some types of HPV infections such as common warts generally regress spontaneously over extended periods of time, and thus patients that seek treatment do so for the relief of temporary pain or discomfort or for cosmetic reasons. These warts are detrimental to the bodily beauty and are deemed to be undesirable by being unattractive, but which in the vernacular do not constitute illnesses.

Current treatment for HPV infection is extremely limited and inconclusive. None of the various therapies for the treatment of HPV infections is considered truly effective as they typically fail to totally cure the lesions and do not prevent recurrence. Part of the explanation for the lack of unified treatment strategies for controlling or curing patients of papillomavirus infections is because they are type specific; a composition that is very effective in treating one type may be completely ineffective in treating another. This is in addition to the inability to grow the virus in vitro and thus develop a convenient and reliable assay to identify efficacious drugs.

Current modalities for the treatment of viral-induced tumors may either be mechanical, antiviral, or immunological. They involve the removal of the tumor by either: (1) surgical intervention (laser or operative); (2) the application of organic acids, such as glacial acetic acid and/or salicylic acid and lactic acid to "dissolve" or "burn" the tumor away; (3) the injection into the tumor of an anti-tumor vaccine prepared from ground tumors; (4) Necrotization by means of electrocauterization or cryocauterization (cryotherapy) with liquid nitrogen, and to a lesser extent, (5) the use of a drug, such as podophyllin, fluorouracil (5-FU), Bleomycin, and interferons, (6) gene therapy using one or more DNA synthesis inhibitors, or (8) using natural ingredients like sandalwood oil, shark cartilage extract, and others.

Over-the-counter compositions currently being marketed for wart removal comprise an effective amount of salicylic acid as main active ingredient. One such product is Occlusal RTM-HP marketed by the GenDerm Corporation of Lincolnshire, Ill. These products are 17 to 40% solution of salicylic acid in a vehicle which dissolves the wart away upon topical application for a couple of weeks. The Shering-Plough Company of Memphis, Tenn. produces and markets a product known as Duo Film® which is a patch containing salicylic acid. The product literature recommends that the wart be washed and dried prior to the application of a medicated patch which contains 40% salicylic acid. This patch is then covered with an additional bandage and the procedure is repeated every 48 hours until the wart is gone, which sometimes takes up to 12 weeks. Other products based on 17% solution of salicylic acid as active ingredient are marketed by Rite Aid Corporation among others for removing corn, callus and wart. Dr Scholl's Clear Away Gel marketed by Schering-Plough Healthcare Products, Inc. is a 17% solution of salicylic acid with aloe extract in alcohol and ether. DuoFilm liquid wart remover and DuoPlant gel wart remover for feet both marketed by Schering-Plough Healthcare Products, Inc. also comprise 17% solution of salicylic acid with castor oil in alcohol and ether. CompoundW gel wart remover marketed by Medtech is a 17% solution of salicylic acid with Camphor and Castor oil in alcohol.

All of these over-the-counter products presently marketed for wart removal have one thing in common. They all comprise an effective amount of salicylic acid which dissolves the wart away through topical application which can result in significant local side effects such as scarring and necrosis of the tumor and the surrounding tissue. In addition, none of these products present an antiviral course of action, so desirably needed in the market, and the course of treatment sometimes takes up to 12 weeks.

There are about 490 U.S. and foreign patents claiming methods of treatment of the human papillomavirus induced lesions (warts) and diseases. None of these discloses or even remotely suggests a therapeutic or prophylactic effect of vertebrate kidney or extract(s) or composition(s) or derivative(s) thereof as being useful for the treatment of human papillomavirus-induced tumors or warts. Due to the large multitude of these patents, only representative examples are discuss herein below. The teachings of these patents are incorporated herein by reference.

U.S. Pat. No. 4,891,227 (1990) to Thaman, et al. discloses antiviral compositions comprising containing salicylic acid as main component for treating warts. U.S. Pat. No. 4,595,591 (1986) to Mardi, et al. discloses using acids to remove or "burn out" cutaneous lesions, warts and the like including dilute nitric and nitrous acid. As is well known, however, the treatments with acids and caustic agents often leave more or less ugly scars.

About 80 cumulative U.S. patents to Yu, et al. of which U.S. Pat. No. 6,335,023 (2002) is referenced herein, claim therapeutic action of anti-wrinkle agents for treating warts comprising administering to the infected area of the skin of a human compositions containing one of the following compounds as a main component; some halogenated acetic acids (10%), alpha hydroxyacids, beta hydroxy acids, glycolic acid, glycalic acid, lactic acid, citric acid, glucuronic acid or glucuronolactone, glucoheptonic acid, 2-hydroxycarboxylic acids and related compounds, citramalic acid, alpha hydroxyacids, alpha ketoacids, benzilic acid, mucic acid or mucolactone, galacturonic acid or galacturonolactone, tropic acid, galactonic acid or galactonolactone, saccharic acid or saccharolactone, mandelic acid, gluconic acid or gluconolactone, isocitric acid, ethyl pyranate, ribonic acid or ribonolactone, quinic acid or quinolactone, malic acid, 2-phenyllactic acid, 3-phenyllactic acid, 2-phenyllactic acid, methyllactic acid, tartaric acid, citramalic acid, gulonic acid or gulonolactone, pantoic acid or pantolactone, combinations of alpha hydroxyacids and/or alpha ketoacids, methyl pyruvate, ethyl pyruvate, alpha hydroxyacid esters, hydroxycarboxylic acids and/or ketocarboxylic acids, oligosaccharide aldonic acids, and hydroquinone.

Several patents disclose compositions effectuating treatment of papillomavirus lesions (warts) having natural ingredients as main component. U.S. patent application Ser. No. 20,010,051,184 (2001) by Heng, Madalene C. Y. discloses compositions comprising curcumin. U.S. Pat. No. 4,774,229 (1988) to Jordan discloses compositions comprising plant extracts from zygophyllaceae. U.S. Pat. No. 6,063,381 (2000) to Staggs discloses compositions comprising pungent botanicals. EP. Patent no. 0842660 (1998) to Cheng et al. discloses compositions comprising camellia sinensis extract. WO. Patent no. 9964029 (1999) to Kosovsky discloses compositions comprising Bactris plants.

U.S. Pat. No. 6,132,756 (2000) to Haque, et al. discloses a composition for the treatment of warts, skin blemishes and other viral-induced tumors comprising sandalwood oil. The method is limited to treatment of only certain types of warts.

U.S. Pat. No. 6,028,118 (2000) to Dupont, et al. discloses methods of using extracts of shark cartilage having anti-angiogenic, anti-tumoral, anti-inflammatory and anti-collagenolytic activities resulting in the regression of warts. The extracts are claimed to have no offensive effect on normal body functions.

U.S. Pat. No. 4,315,916 (1982) to Likens, et al. discloses a compound derived from dried bittersweet root bark combined with zinc chloride to form a salve which is topically applied to remove unwanted growths from the skin like warts.

U.S. Pat. No. 5,500,359 (1996) to Boyer, et al. discloses Method for producing a therapeutic composition for papillomavirus-induced tumors with aspergillus niger extract. Cumulative patents also to Boyer, et al. of which U.S. Pat. No. 5,662,903 (1997) is chosen as an example discloses a composition for the treatment of viral-induced tumors comprising an Aspergillus fermentation extract or a derivative thereof in a pharmaceutically acceptable carrier. While such therapy reduced tumor growth by about 25%, it also resulted in a widely spread skin "rashes" (red, lumpy areas) after a few weeks of administration, hypersensitivity, as well as other minor reactions. Skin rashes observed are reminiscent of red skin and itchiness which is observed in regressing warts in patients.

U.S. Pat. No. 5,073,630 (1991) to Nunes, et al. discloses a polymeric anhydride of magnesium and proteic ammonium phospholinoleate with antiviral, antineoplastic and immunostimulant properties. This antiviral agent was produced in the cell-free filtrate of a selected line of Aspergillus sp. That compound is insoluble in water and possesses a high molecular weight. In addition, the production of this antiviral agent from a selected line of Aspergillus sp is problematic and costly.

Cumulative U.S. patents of which U.S. Pat. No. 6,197,808 (2001) to Cheng, et al. is referenced herein disclose a composition for the treatment of HPV-infected condyloma acuminata which comprises containing tea catechin as a main component. The method is claimed effective only for condyloma acuminata and not other types of HPV infections like common warts of the hand, face, and foot.

The medical contributions of animal and livestock organs have been known for many years. Epinephrine from cattle adrenal glands, for example, is used to relieve some symptoms of hay fever, asthma and some allergies. It is also used as a heart stimulant in emergencies and to prolong the effect of local anesthetic by dentists. Thrombin from cattle blood helps blood clotting. It is also used in skin grafting. Liver extract is sometimes combined with folic acid and injected to treat various types of anemia. Insulin derived from cattle pancreas, is used to treat diabetes. Glucagon helps counteract insulin-shock. Other medical products from cattle include rennet, epinephrine, thrombin, heparin, TSH, ACTH, cholesterol, estrogen, and thyroid extract. The medical contributions of young to adult hogs include heart valves that are used in valve replacement surgery in humans of all ages. Pig skin is used as replacement of human skin. Gelatin is used for capsules and pills. Thyroid extracts are used to regulate the rate of metabolism in humans. Other extracts are used to treat low calcium and phosphate levels and regulate heart beat. Pancreas extracts are the source of insulin. Other medical products from hogs include cortisone, Norepine, plasmam blood fibrin, estrogen, relaxin, bum dressings, pepsin and oxytocin.

Patents that disclose compositions effectuating treatment of papillomavirus lesions (warts) having animal organs as main component include U.S. Pat. No. 6,165,481 (2000) to Kaiya, et al. disclosing using pure squalane from animal oil or fat, and U.S. Pat. No. 6,028,118 (2000) to Dupont, et al. disclosing using extracts of shark cartilage.

U.S. Pat. No. 5,997,549 (1999) to Sauceda, et al. discloses a wart removing tool which comprises an abrasive carbide pad mounted at one end of an elongated handle. Wart is removed by mechanically scrubbing it with the tool twice a day for about four to ten weeks. It is believed that this application causes an interaction between the carbide and possibly the cobalt contained within the carbide which functions to neutralize the virus that creates the wart. Although the described technique does remove the lesion, it does not eradicate the latent virus and reoccurrence is imminent.

U.S. Pat. No. 6,312,735 (2001) to Niazi, et al. discloses a method for the removal of all types of human and animal skin warts using a technique of cauterization wherein slaked lime is applied to wart and then the surface of wart is ruptured mechanically with the stub of the stem of a betel leaf. The wart is usually removed within few minuets after one or more applications. Although the described technique does remove the lesion, it does not eradicate the virus and reoccurrence is imminent.

U.S. Pat. No. 5,532,215 (1996) to Lezdey, et al. discloses a method for inhibiting viral proliferation by preventing or inhibiting viral replication or killing the virus on contact. The method uses serine protease inhibitors, their analogs, salts, conjugates or derivatives.

U.S. Pat. No. 5,492,935 (1996) to Yu et al. discloses a method of alleviating warts, comprising administering topically or by subcutaneous injection to involved areas of the body a retinal compound and its derivatives. The method is expensive and requires administration in a professional clinic.

U.S. Pat. No. 6,306,383 (2001) to Crandall discloses a method for the topical treatment of warts comprising a selected protein kinase c inhibitor and an effective penetrating agent selected from lecithin organogel or poloxamer 407 lecithin organogel. The protein kinase c inhibitors may be selected from sphingosine, sphinganine, phytosphingosine, N-Acetylsphingosine, N-Hexanoylsphingosine, N-Octanoylsphingosine, curcumin, tetrahydrocurcumin, curcuminoids or apigenin. The method is expensive and requires administration by a professional.

U.S. Pat. No. 6,309,662 (2001) to Buchanan discloses a method of perorally treating warts caused by the papillomavirus in humans wherein ciprofloxacin hydrochloride is administered perorally twice per day to stimulate immune response. The effective generation of this response is solely dependent upon the patient's immune system and health status and thus may not always be effective.

These references and patents make no suggestion or disclosure that the kidney from vertebrates or any composition or extract thereof would be effective or as having medical contribution in treatment of human papillomavirus-induced tumors and diseases such as warts. The present invention falls along the same line, utilizing kidney from vertebrates or extract or active component thereof for treating human papillomavirus induced lesions, tumors, and diseases. The novelty and unobviousness requirement have, therefore, been duly met by the present invention.

While being useful for removing the viral-induced tumor, the current treatment modalities presently used nonetheless suffer from one or more of the following drawbacks: (1) they can result in the destruction of healthy uninfected tissue; (2) they can result in scarring and disfigurement; (3) they can result in pain or discomfort to the mammal being treated thereby; (4) they can result in significant local, and at times, systemic side effects such as necrosis of the tumor and the surrounding tissue and can result in a secondary infection which may require treatment with an antibiotic; (5) they do not always result in the destruction of latent viral DNA which may be maintained in surrounding tissues leading to frequent recurrences of the tumors, therefore, incomplete resolution; (6) They require costly professional assistance; and (7) they require a long course of treatment which sometimes could takes up to several months.

People have had skin wastes, blemishes, and warts removed by surgical operations or irradiation with laser light in specialized hospitals. However, such treatment incurs expenses, takes much time, and sometimes leaves scars on the skin. In the past, a vacuum pump was directed to the infected vaginal or rectal area for the removal of the plume or laser mist. Furthermore, problems have arisen by the escape of said laser mist causing obscurity of the surgical area viewed by the operating doctor as well as rise of such plume or laser mist in the nostrils of the doctor performing laser surgery resulting in the causing of irritation, sometimes developing in a venereal wart in his nasal passages. Germs and viruses that linger in the air following the laser operation may also settle into the open wounds of the next patient being operated on, potentially resulting in the transmission of that disease to the next patient. As of the present time, it remains unclear to what extent these airborne viruses pose a threat to later patients of the operating room although it is known that HPV DNA virus does survive the laser surgery procedure and may pose a health risk if allowed to linger in the operating room.

Electrosurgical procedures (electrocautery) include use of an electrosurgical generator with an electric needle for wart removal. The disadvantage of removing warts with an electric needle is that it destroys the wart by "burning" which is very painful and produces a rather unsightly appearance until the area heals which was occupied by the wart. This procedure also results in the burning of tissue, rather than its vaporization, as from laser procedures creating permanent unsightly scars. Also, at times, this technique does not result in elimination of the virus in the tumor resulting in the wart regrowing. Furthermore, this technique does not result in elimination of the latent viruses in the surrounding tissues thus providing incomplete resolution and frequent reoccurrences of warts outbreaks. The plume of airborne contaminants generated during electrocautery may further include germs and viruses that linger in the air following the operation and may also settle into the dermatologist or the open wounds of the next patient being operated on, potentially resulting in the transmission of the viral DNA to the next patient.

Treatment with cryocauterization (cryotherapy) has found difficult to obtain good results when precise placement of the cotton bud is needed, e.g. for small warts; and when the treatment site is difficult to reach; and when the treatment site is large. In addition, cryocauterization destroys healthy hair follicles resulting in unsightly hairless areas in the treated skin. Scarring of the surrounding healthy tissues is also sometimes experienced when the cryogenic liquid is not properly applied. For example, the middle knuckle of the left hand of a 42 year old woman was injured by the removal of a small wart with liquid nitrogen. Two months following the liquid nitrogen insult, the injured area (approximately 1 cm in diameter) was characterized by scar tissue raised several millimeters above the surrounding normal skin.

U.S. Pat. No. 6,372,218 (2002) to Cummins discloses treatment with interferon, of particularly against refractory genital warts which has so far been the only treatment with an antiviral mode of action. This method has only been partially successful with cure rates in the range of about 36% compared to spontaneous remissions of 3%.

U.S. Pat. No. 5,705,518 (1998) to Richter, et al. discloses using phototherapy for removing laryngeal papillomatosis tumors. While such phototherapy reduced tumor growth by about 50%, it also resulted in a generalized skin photosensitivity for at least six weeks, as well as other minor reactions. Furthermore, despite the apparent success of this technique, the presence of latent viral DNA is nonetheless still maintained in the surrounding tissues.

U.S. Pat. No. 6,306,397 (2001) to Edwards, et al. and U.S. Pat. No. 6,350,451 (2002) to Horn, et al. have shown in their immunological studies in animals that the production of neutralizing antibodies to papillomavirus antigens prevents infection with the homologous virus. These however have proven limited success because papillomaviruses appear to be type-specific immunogens in that a neutralizing immunity to infection to one type of papillomavirus does not confer immunity against another type of papillomavirus. The development of effective papillomavirus vaccines has been slowed by difficulties associated with the cultivation of papillomaviruses in vitro. The development of an effective HPV vaccine has been particularly slowed by the absence of a suitable animal model. Furthermore, some immunogenic medications that function by increasing the immune system of the patient for therapy or prophylaxis against PV infections do not work especially in the case of immune deficient individuals such as AIDS patients. Accordingly, there is need in the medical community for medicaments and methods for prevention and treatment of such viral infections that do not depend on the immune system of the patient.

This wide range of essentially destructive therapies and a few nondestructive therapies indicates that none have been found to be outstandingly effective. Most of these therapies have been used for years, and are painful for adults and not tolerated by children. Some can even result in scarring without demonstrating good long-term clinical results. The greater incidence of anogenital warts in the general population includes children. Children have very limited treatment options. Furthermore, most standard therapies are ablative and caustic and treat only the visibly appearing warts and do not treat the underlying virus. While some therapy reduce tumor growth they also result in a widely spread skin "rashes", hypersensitivity, as well as other minor reactions after a few weeks of administration. Furthermore, HPV infection has a high rate of recurrence, and a complete cure is difficult unless treated constantly.

Accordingly, it can be seen that there remains in the medical community a great, but as of yet unfulfilled, need for prophylactic or therapeutic methods and compositions of matter capable of preventing and treating viral-induced tumors (such as warts) in mammals without either destroying healthy uninfected tissue, causing significant systemic side effects, causing scarring or disfigurement of and/or discomfort to the mammal treated therewith, and which results in the destruction of latent viral DNA which may be maintained in surrounding tissues, so that instances of incomplete resolution and frequent recurrences of the tumors are reduced. It can further be seen that there also remains a need for methods for providing such prophylactic or therapeutic compositions, as well as methods for the use of such prophylactic or therapeutic compositions which does not depend on the immunological condition of the patient or health status, has a high degree of safety and is convenient for the prevention and treatment of viral-induced tumors in mammals. The present invention fills that need of the medical community.

ADVANTAGES OF THE PRESENT INVENTION

The present invention provides a simple way to treat warts in humans and a variety of diseases in other animals with compounds that are inexpensive and easy to find and make. It imparts optimum therapeutic or prophylactic strategy of HPV infection that accelerates the induction of a strong virus specific antiviral response to effectuate wart regression with less pain and that could be well-tolerated by adults and children. There is no risk or danger of side-effects from the treatment for HPV tumors (warts) with the composition of the present invention which may be taken for long periods of time having the kidney of vertebrates as the main component thereof since the main component is a natural substance derived from mammal which is commonly consumed regularly. One major benefit of the present invention is that the antiviral composition does not destroy healthy uninfected tissues or results in systemic or local side effects such as irritation, necrosis of tissue surrounding the wart, allergic rashes, scarring, disfigurement or discomfort to the human treated therewith. Moreover this medication may be easily applied to or inserted in the infected area by the patient themselves. Therefore, the composition of the present invention for a treatment of HPV tumors has a very high potential for practical use.

In preferred embodiments of the present invention is preferably capable of: (1) suppressing tumor growth, e.g., in a tumor cell; (2) suppressing growth of papillomavirus-infected cells, e.g., HPV-infected cells; (3) inhibiting growth of a papillomavirus-infected cell, e.g., an HPV-infected cell, e.g., a high-risk HPV infected cell, e.g., and HPV-16, -18, -31, or -33 infected cell, e.g., a bovine papillomavirus (BPV)-infected cell; (4) inhibiting infection of a cell by a papillomavirus, e.g., an HPV, e.g., a high-risk HPV, e.g., and HPV-16, -18, -31, or -33, e.g., a bovine papillomavirus (BPV); (5) inhibiting transformation of a cell by a papillomavirus, e.g., an HPV, e.g., a high-risk HPV, e.g., and HPV-16, -18, -31, or -33, e.g., a bovine papillomavirus; or (6) inhibiting immortalization of a cell, e.g., a human cell, by a papillomavirus, e.g., an HPV, e.g., a high-risk HPV, e.g., and HPV-16, -18, -31, or -33, e.g., a bovine papillomavirus; (7) inhibiting the growth of, or diminishing the size of a wart.

BRIEF SUMMARY OF THE INVENTION

The method of this invention is specifically directed to prophylactic and/or therapeutic antiviral compositions for the prevention and treatment of viral-induced tumors, lesions and diseases in mammals comprising as main component at least one constituent of kidney, or portions, extracts, or compounds thereof, as well as derivatives, metabolites or precursors of such compounds, and pharmaceutically acceptable salts or preparations of any of these compounds, collectively defined herein as the "active compounds of the present invention", and wherein said kidney is obtained from at least one vertebrate preferably from ruminant species and more preferably sheep and goat.

The invention also provides for methods of preparing the said antiviral compositions from said kidney or portions thereof as an aqueous extract, a powder, or other forms suitable for therapy or incorporation into a pharmaceutical or cosmetic product, using extraction, filtration, concentration and other purification steps in any sequence or combination deemed suitable for the purpose intended and which favor the maintenance of biological activities.

It is therefore an object of the present invention to provide pharmaceutical or cosmetic preparations from said kidney, derivatives, or antiviral compositions that are useful for treating viral infections such as human papillomavirus diseases. Another aspect of the present invention is directed to a simple method for providing prophylactic or therapeutic treatment of viral-induced tumors in humans which permit easy removal of skin disorder such as warts in a beauty shop or at home.

There is further disclosed a method for the prevention and treatment of viral (PV) induced lesions, tumors, cancers and infections comprising the parenteral application of the antiviral composition of the present invention, or a pharmaceutical or a cosmetic composition containing at least one constituent of said antiviral composition to the affected area of the body for a period of time and at a sufficient concentration to eradicate the papillomavirus from the infected tissues of the mammal in need of such therapy so as to prevent recurrence of these tumors. It is proposed that the continued use of the active compounds of the present invention would be effective for the prophylactic treatment of viral tumors and eradication of HPV and DNA viral infections.

DETAILED DESCRIPTION

I, the present inventor looked for a natural substance which has no side-effects, may be safely applied for a long period of time by the patient themselves and is notably effective in treating viral induced tumors such as warts; and after extensive testing I discovered that the kidney from vertebrates is effective and thus the present invention was developed.

The initial discovery of the inventor was based upon the use of a crude kidney from vertebrates such as ruminant species and more specifically sheep and goat. The inventor has found the raw kidney of sheep and the juices therein to be effective in removing warts, which is a manifestation of viral infection, thus concluded the sheep kidney to have preventing and treating effect on viral induced epidermal tumors. The inventor also concluded that raw kidney or extract or compositions thereof, from vertebrates and preferably from ruminant species and more preferably from sheep and goat, is to contain active components useful for the prevention and treatment of viral-induced tumors, infections, cancers and diseases in mammals such as humans.

Most interest has been drawn to formulations for use in dermatology. This interest comes from the observed activities of the renal extracts. In this respect, the observed anti-tumor proliferating and direct in vitro anti-tumor proliferating activities have been considered as opening avenues to the use of the vertebrate kidney or its extracts in compositions and methods for the reduction of skin atrophy (the regression of warts). Furthermore, since the vertebrate kidney and liquid extract thereof has been successfully tested in wart treatment, compositions and methods for treating diseases or conditions of tumor proliferation are under the scope of this invention.

As will be set forth below, the inventor have elucidated that the sheep renal extract is the agent with the outstanding utility for treating and/or preventing PV infections, tumors, and diseases such as warts.

It is a primary object of the present invention to provide a method of treating a localized solid tumor, papilloma or wart in mammals such as humans, comprising introducing an effective amount of an antiviral composition directly into said tumor or papilloma. In addition to its use in human medical therapy and/or prophylaxis, the active compound can be administered to other animals for prevention and treatment of viral diseases, e.g. to other mammals. The method comprises administering to the host in need of such therapy the antiviral composition of the invention to provide an effective antiviral amount of the active compound. A wide variety of papillomas and warts can be treated by the same therapeutic strategy. Representative examples of papillomas include squamous cell papilloma, choroid plexus papilloma and laryngeal papilloma. Representative examples of wart conditions include genital warts, plantar warts, epidermodysplasia verruciformis (EV) and malignant warts.

Preferably, the prophylactic and/or therapeutic antiviral compositions of the present invention constitute as main active component kidney from at least one vertebrate or portions or extracts or compositions or derivatives thereof termed herein "the composition of the present invention". It is further preferred that these kidney or portions or extracts or compositions or derivatives be from ruminant species. A preferred kidney is a ruminant species kidney, with kidney from sheep, lamb, or goat being especially preferred of all. If desired, the compositions of the present invention may be compositions which are either derivatives of and/or have been derived from the kidney or portions or extract(s) thereof disclosed herein. If desired, the method may further include the preparation of a derivative of the kidney or extracts.

In further accordance with the teachings of the present invention, disclosed herein are methods for further purifying and isolating the therapeutically active chemical or biological ingredient(s) from said kidney or portions thereof for preparing the said prophylactic and/or therapeutic antiviral compositions as an aqueous extract, a powder or other liquid, solid, or vapor forms, suitable for therapy or incorporation into a pharmaceutical or cosmetic product. Such methods include but are not limited to at least one of the following refining techniques such as grinding, pasting, drying, freezing, crystallization, powdering, filtration including using membranes, adsorption, leaching, extraction including using supercritical extraction, centrifuge, concentration including using evaporation and using vacuum, all types of distillation including using thin film distillation, vacuum distillation, extractive distillation, reactive distillation, and steam distillation, and other purification steps in any sequence or combination deemed suitable to obtain the antiviral composition from kidney in the form of liquid, solid, vapor, etc. and which favor the maintenance of biological activities.

According to the teachings of the present invention, the prophylactic and/or therapeutic antiviral compositions are obtained in such a manner that does not denature the valuable components and preserves the integrity and activity of the biologically active renal compounds. Moreover, the simple methods are to yield sufficient amounts of active components, and recover all or a sufficient yield to show detectable activity.

In a particular aspect of the present invention, disclosed herein are methods for the use of the compositions of the present invention for the prevention and treatment of human papillomavirus-induced tumors in mammals. These methods further include administering a therapeutically-effective amount of the composition to a mammal in need thereof. Such administration may, in the case of a prophylactic treatment, be on that area of the mammal on which it is anticipated that such preventive treatment is needed or, in the case of a therapeutic treatment, be directly on the viral-induced tumor of the mammal in need of such treatment. Preferably, such application of prophylactic and/or therapeutic compositions may be topical or subcutaneous.

It is still further preferred that the compositions of the present invention include the said kidney or portions or extracts or compositions or derivatives thereof in a pharmaceutically-acceptable carrier, so that a prophylactic and/or therapeutic composition is provided for the prevention and treatment of viral-induced tumors in mammals.

It is therefore a further aspect of the present invention to disclose herein are methods for the use of the compositions of the present invention for the preparation of prophylactic and/or therapeutic medical, pharmaceutical, or cosmetic products or an adjuvant composition suitable for topical or subcutaneous application for the prevention and/or treatment of viral-induced tumors in mammals such as warts. In a preferred embodiment, an anti-fungal and/or an anti-bacterial are in addition added.

It is a further a primary object of the present invention to provide prophylactic and/or therapeutic compositions and methods of using them for the prevention and/or treatment of viral-induced tumors in mammals which compositions and methods neither destroy healthy uninfected tissue, nor result in either significant systemic side effects, scarring, disfigurement or discomfort to the mammal treated therewith, and further which result in the destruction or neutralization of latent viral DNA which may be maintained in surrounding tissues, so that instances of incomplete resolution and frequent tumor recurrence are greatly reduced if not completely eliminated.

It is a further a primary object of the present invention to provide a treatment which is simple, safe, inexpensive, abundant, and easy to prepare and for the patient to take, for example a medication which can be applied to the affected area by the patient themselves showing good results in a relatively short period of use and having no side-effects. There is further no need to rub off the surface of the wart on mechanical manipulation as the lesion shrinks and disappears by itself leaving no trace of infection what so ever.

It is a further primary object of the present invention to provide an effective therapeutic and/or prophylactic antiviral composition or medicament which targets the virus and is not dependent upon the patient's immune system or health status which might be critical in the case of immune-deficient individuals such as AIDS and allograft patients.

These and further objects and advantages of the present invention will become readily apparent upon a reading of the following invention in conjunction with the examples thereof.

DESCRIPTION OF METHODS OF PREPARATION

The present invention relates to the prophylactic and therapeutic action of the kidney and active components thereof and to a method of producing the same. Renal compounds of the present invention having anti-tumor activities have been obtained from ruminant animals by several processes. The process comprises the steps of obtaining a homogenate of kidney in an aqueous solution, this homogenate being separated in a solid fraction (solid extract) and a liquid fraction (liquid extract). Further fractionation of this extract can lead to the preliminary characterization of some of its active components. Due to the multiplicity of biological activities of the total renal extracts, it can be used for treating numerous diseases or conditions such as those having components of tumor proliferation. These extracts have no offensive effect on normal body functions. Therefore, these renal extracts have a very promising prophylactic and therapeutic value. The process for the intention of renal extracts is simple and efficient. The unexpectedly valuable products obtained by this process are therefore an indication of a new and non-obvious process.

The prophylactic and therapeutic compositions of the present invention are provided by, first, harvesting the kidney from a vertebrate such ruminant species. Preferred is kidney from ruminant species such a sheep, lamb, or goat. The precise biomass medium, procedure, pharmaceutical composition, and concentrations to utilize will vary according to the microbe (PV-type) to be treated therewith, as is well within the skill of the art to ascertain.

The antiviral composition of the present invention in crude form can be produced in any means from the kidney of a vertebrate. Methods of obtaining and preparing these compositions will be explained in more detail with reference to the following examples which are in no way meant to limit the scope of the invention.

In a specific embodiment, kidney has been obtained from healthy sheep. Any fat and connective tissue has been removed by scraping with ethanol-treated scalpels and scissors. The kidney is then vacuum-packed in plastic bags and frozen to −60° C. to preserve and disinfect from germs, viruses, and bacteria until further use. Clean kidney may be used fresh, frozen, or thawed to 4° C. It is then passed through the pores of an ethanol-aseptized meat grinder together with an adequate volume of distilled water. An equal quantity by weight or volume is exemplary but can be altered without bearing any effect on the yield of recovery of valuable components. A low volume is preferred since it is more convenient to manipulate than unnecessary high volumes from a practical point of view.

Many aqueous solutions (salt solutions, for example) could be used in lieu of water to extract extracellular compounds from the biomass medium. When recovery of a plurality of hydrosoluble activities is contemplated, working at a near neutral pH (5.0 to 8.0) and non-denaturing conditions are preferred to avoid lysis or denaturation of some of the kidney active components. The behavior of unknown proteins in aqueous solvents is not predictable; some may be more "comfortable" in an acidic pH, some at a basic pH. Furthermore, some proteins may be extractable in mild denaturing conditions, if such denaturation does not irreversibly affect the re-naturation of these proteins in aqueous solutions. For sake of clarity, any condition of extraction which is compatible with the preservation of biologically active renal component is under the scope of this invention.

Other solvents may also be used in which solvent is inert to the reaction and can easily be separated from extract such as saturated hydrocarbons of n-hexane, isooctane and so forth. Therefore, taking all these factors in consideration, performing a process of extraction of renal active components in pure water has been shown to be a judicious choice to recover with a very good yield, components having a yet to be define structure and behavior.

Any variation in the preparation of kidney prior to its extraction may be used as long as it does not substantially affect the activity of the product of interest (a total liquid and solid extract or a particular fraction thereof for example). Some active components may resist proteolytic digestion as taught by Balassa et al. (1989) in U.S. Pat. No. 4,822,607, while others may not resist such treatment. Therefore, to produce a liquid extract containing as much as possible of all the hydrosoluble active components to which are assigned separate activities, such a digestion step during the extraction procedure should preferably be avoided or carefully monitored to prevent extensive hydrolysis or proteolysis.

The blend, kidney and water, is then made homogenized by agitation preferably at a maximal speed in a commercial blender at about 4° C. during 2 minutes. It is foreseen that the speed and time of the agitation as well as the volume of aqueous solution may influence both time and yield of extraction. Therefore, a reasonable range of homogenization speed and time can be utilized as long as it does not cause denaturation of active components, due to temperature increase for example among other reasons. Preferably the temperature should be maintained to below about 4° C., to avoid any degradation of active components by endogenous enzymes or bacteria, when no enzyme or bacteria inhibitors are used. Ideally, a temperature close to 0° C. should be sought. Since normally such experimentation is made in a cold room, wherein the temperature can be maintained between 4 and 10° C., this range of temperature is judged acceptable in the present process. For sake of clarity and brevity, the terms "about 4° C." is hereinbelow used to designate (and not restrict) this acceptable range of temperatures.

Alternatively, the blend can be homogenized simply by shaking vigorously for about a minute. Of course, the same acceptable ranges of time and temperature discussed for the obtention of the first grinded kidney equally apply. The size of the particles after homogenization does not need to be ultra small. Therefore, the need to pulverize the kidney before extraction can preferably be avoided. Indeed, pulverization of kidney in the form of a powder before aqueous extraction may on the contrary denature valuable activities, especially when such pulverization is performed in a heat-dry state.

The homogenate can be centrifuged preferably for about 10 minutes at about 4° C., which step is one way to separate quickly and efficiently a supernatant from a pellet. Utilizing centrifugal force to flow down solid extract by gravitation a clear liquid (supernatant) is obtained which can be filtered easily or just harvested leaving the solid extract undisturbed. The cell biomass still contains the active ingredients and may also be used for the purposes of the present invention. Variation and adjustment of these parameters are well within the knowledge of the skilled artisan, merely depending on the volume of homogenate and of the equipment used.

Alternatively, the blend can be simply left for about 24 hrs to separate by the force of gravity. The supernatant can be filtered on a standard filter paper, if desired, eliminating the unsolubilized material and particles susceptible to affect the performance of further purification processes or product quality. The final filtration process is not detrimental for the said medicament to function but rather to have a homogeneously desirable shape. The first fraction is herein defined as the "renal liquid extract" and the second fraction as the "solid renal extract". The aqueous volume obtained is higher than the starting volume of water, suggesting that a part of the liquid content of the kidney itself has been harvested.

Furthermore, the liquid filtered extract may then be used as such, or it may be further processed, such as by being concentrated, so that a suitable derivative thereof is provided. The method may further include a fractionation, e.g. vacuum distillation step, which would further enrich an extract in active components. The thin film distillation may also be employed in the method of the present invention as a refining method, so that, for the purpose to carry out the thin film distillation a thin film distillation apparatus or thin film evaporator or the like can be employed. In addition, filtration and/or thin film distillation may in addition be used for the purpose of removing impurities. The distillation is characterized in that the operation can be done at a low temperature to avoid the decomposition and deterioration of active ingredients.

The method of the present invention further allows producing a powdered crude kidney without any extraction. A powder preparation may be obtained by drying the said kidney or portions or extracts thereof in a manner that is not denaturing to the active principals then grinding the resulting dried kidney to a fine powder. The renal extracts may also be dried using techniques including but not limited to, for example, spray-drying or freeze-drying to produce a powder suitable for topical application. The resulting solid extract may also be lyophilized (freeze dried) for 24 to 48 hours.

A tincture may be prepared by soaking of ground kidney in an equal weigh of solution containing approximately 50% ethanol and 50% water. Pure ethanol and other pharmaceutically acceptable alcohols and solvents such as acetone, chloroform, vinegar (acetic acid) may also be used. The mixture should be agitated, at least occasionally, over about 1 hour a period, with maximum extraction being obtained after about 24 hours which is more preferred. Allowing the mixture to sit over night produces excellent results. Before use, the residual ground kidney may be strained off, and liquid tincture saved for use. It is anticipated that the solid extract may also have activity.

The antiviral composition in the form of liquid drops suitable for topical application may be obtained by concentrating the renal extract by reducing tincture through heat, or passive evaporation.

An infusion of renal extract may be prepared by soaking approximately 1 kg of commercially available kidney to one liter (1 quart) of water of sensibly comfortable temperature. Infusion should be allowed to soak preferably for at least one hour before use with 24 hours being more preferred for best results. According to preference, infusion may, or may not be strained to remove residue before use.

A tea of is a more potent version of infusion above, using about 1 kg of ground kidney for each liter of sensibly comfortable water. Tea may also be prepared from boiling water, or itself be boiled in water before use. Boiling the biomass in water assures complete release of active agents.

If desired, delivery of active principals in the above preparations can either be in pure form or admixed with other substances like preservatives or antibacterial or antifungal agents including but mot limited to alcohol, methyl hydroxy benzoate, and propyl hydroxy benzoate, or dispensing agents including but not limited to creams, gels, ointments, and so forth, or using inert substances including but not limited water or solvents and so forth.

If not used immediately, the renal liquid extract or composition(s) or derivative(s) thereof is preferably protected from light to preserve photolabile substances in sterile bottles and stored at −60° C. for a maximum period of three months.

The renal liquid extract may lose some of its activities if preferably lyophilized. However, the addition of stabilizers or protective agents as known in the art prior to lyophilization may preserve sensitive activities and make possible the administration of higher doses of the renal extract in the dry state.

If not to be used immediately, the liquid filtered extract and/or derivative thereof is, preferably, refrigerated until the use thereof and/or may further be admixed with at least one chemical with an antiviral, antimicrobial, antibacterial, or antifungal course of action or other chemical(s) to prevent disintegration and contamination. Preferably, such refrigeration is done at about −60° C.

If long-term storage is desired, the liquid filtered extract or derivative thereof may then be vacuum concentrated, followed by a clarifying filtration. The filtrate or derivative thereof may then be freeze-dried. The resulting freeze-dried powder of the liquid extract or derivative thereof is very soluble in water. When use thereof is desired, the freeze-dried powder may be re-dissolved in a liquid such as water and/or a pharmaceutically-acceptable carrier.

The kidney or the thus obtained extract thereof is quite suitable as medical, pharmaceutical or cosmetic products and as a raw material for producing them. It is especially suitable as a raw material for producing these products which are brought into contact with skin in use. The medical or pharmaceutical products are exemplified by several kinds of creams, ointments, and disinfectants. The cosmetics are exemplified by several kinds of makeup, cosmetic foundations, eye shadows, mascaras, blushers, perfumes, lipsticks, skin nutrient oils, hair ointments, milky lotions, cosmetic creams, and bathing agents.

The prophylactic and/or therapeutic compositions may further be formulated as desired for topical or subcutaneous application on either the area of the mammal to be protected or on the afflicted tumor (wart) of the mammal in need thereof. Such formulations include but are not limited to liquid compositions, such as oil-based ointments (such as a cream, jelly, emulsion); liniments and tincture compositions.

The antiviral component may further be combined with an excipient, extending agent, emulsifier, dispersing agent and so forth. Vaseline is suitable as a base for the ointment. Creams, lotions, soaps, shampoos, detergents, and gels are especially preferred for their ability to keep the prophylactic and therapeutic compositions in prolonged contact with the skin and/or tumor for a sufficient period of time. Further formulations may be in the form of a lipstick balm, embodied in a patch, or directly injected into the wart with a needle.

The pharmaceutically-acceptable carrier may be any such carrier well-known to those skilled in the art. It is preferred that such a carrier be a hydrophilic substance that aids the prophylactic and therapeutic compositions to penetrate the skin. Examples of such carriers include but are not limited to aqueous menthol solutions, water, propylene glycol, lanolin, butyl alcohol, absolute alcohol, isopropyl alcohol, dimethyl sulfoxide, ether ethyl lactate, aqueous solutions of menthol and mixtures thereof. Another example of such a carrier is the well-known "Vehicle N", a composition comprised of ethyl alcohol, isopropyl alcohol, purified water, Laureth-4 (a surfactant) and propylene glycol.

The pharmaceutically-acceptable product may be formulated in any such manner well-known to those skilled in the art and applied to infected areas in its intended manner. None limiting examples may be in the form of a plaster or poultice prepared by mixing ground kidney with water, until it has a paste-like consistency that will assure good adherence to the skin, or cloth to which it is applied.

A lotion, cream, or shampoo preparation may also be obtained by adding to any commercially available shampoo, cream, or lotion a portion of drops or tincture in an amount enough to effectuate the desired treatment. A douche may be prepared from infusion, or tea that is strained of the kidney residue material before use.

An injection may be prepared from a purified version of infusion, tea, drops, etc. administered subcutaneous in a PV infected tissue such as a wart for example. The vaccines used in the present invention may also include both inactivated whole and subunit vaccines as well as toxoids. Moreover, the vaccines employed may be those used to immunize against viral pathogens. Suitable human and veterinary vaccines would include for example, the whole and subunit vaccines for HPV which is a wart virus.

A powder formulation may be prepared from dried kidney in ground form, or extracts mixed and/or bound within a binding powder carrier such as talc. Powder form has a more medical application than the other carriers. If used as a foot powder for example, it is best to fix the renal compounds within a powder binder such as talc, to prevent, or lessen escape of airborn particulate. Powder may be the perfect formulation for preventing wart formation on the foot when used regularly.

If deemed safe, an aerosol formulation may be inhaled in the treatment of throat, and respiratory infections (laryngeal papillomas). In this administration, aerosol is preferably derived from a lower concentration, such as infusion for example. For this reason, aerosol is somewhat limited in its medicinal application.

Vertebrate kidney and any of its active constituents may be administered as a general anti-infective in the treatment of disorders including viral infections and may furthermore be administered in combination with other therapeutic agents in the above formulations of the present invention. Non-limiting examples include adding a topical or subcutaneous anesthetic, such as lidocaine, or benzocaine to pharmaceutical or cosmetic formulations if irritation is a concern to reduce severity. If skin is very dry, emollients may also be added to the formulations.

Concerning medical and pharmaceutical products, the uses for the component of adjuvant composition are especially useful. In the present invention, all the well known medicinal agents used generally for adjuvants can be employed as the components besides the kidney or extract. The adjuvant composition of the present invention may be an auxiliary agent or an antigen to generate antibody and to enhance immunity of cells. Especially when it is mixed with immunogen it may improve or change the immune response, for examples when it is used together with the so-called vaccine or it is used as one component of vaccine. The adjuvant composition according to the present invention may also contain, if necessary, terpenoid, vegetable oil and so forth besides the above-described components. Furthermore, the adjuvant composition can contain a glycopeptide, glycerides, phospholipid, and glycelol. If necessary, an aluminum compound can also be incorporated. Furthermore, it is also possible that an antioxidizing agent such as vitamin E or lecithin is added to the antiviral composition, if it is desirable. Other components such as preservatives and perfumes can be used in the said antiviral composition of this invention.

The antiviral composition of the present invention may sometimes be used as it stands however it is generally preferred to be used in pharmaceutical or cosmetics formulations together with an emulsifying agent and an aqueous medium. Emulsifying agent may be selected from but is not limited to biological surfactants selected from anionic, cationic, non-ionic, and zwitterionic surfactants or combinations thereof. Any method can be employed for preparing the emulsion of antiviral composition of the present invention. For example, lotions, ointments, and creams may generally be prepared by emulsifying renal extracts into oil-in-water (O/W) or water-in-oil (W/O) emulsions using an emulsifying agent and a homogenizer and then supplied for use. The aqueous portion may be pure water or buffered saline with phosphates. Because the composition is intended for parenteral administration, it is preferable to make up a final buffered solution so that the tonicity, i.e., osmolarity, is essentially the same as normal physiological fluids in order to prevent post-administration swelling or rapid absorption of the composition because of differential ion concentrations between the composition and physiological fluids. It is also preferable to buffer the saline in order to maintain a pH compatible with normal physiological conditions. Also, in certain instances, it may be necessary to maintain the pH at a particular level in order to insure the stability of certain composition components. In the present invention, the combination of two or more emulsifying agents, i.e. surfactants, can be used.

Examples of emulsifying agents, buffer solutions and surfactants that may be used in conjunction with the present invention are well within the ability and the knowledge of the person skilled in the art to determine, without departing from the teachings of this disclosure. U.S. Pat. No. 6,165,481 (2000) to Kaiya, et al. discloses a plurality of non-limiting examples the teachings of which are incorporated herein by reference.

The prophylactic and/or therapeutic compositions can be administered, in any suitable manner well-known to those skilled in the art. Such methods can include subcutaneous or intravenous injection. Preferably, this administration is a topical administration, such as by being applied to the surface of the skin or tumor (or afflicted area in need thereof) with the aid of an liquid-dropper, brush, porous applicator (such as cotton gauze, swab, cloth or bandage such Band-Aid™, etc.), roll-top applicator, spray or aerosol, or a liposome or any other suitable application means, as desired.

The prophylactic and/or therapeutic compositions may be administered to the area of infection (wart) in the form of crude kidney or portions or grind thereof. They may also be administered after extracting the active chemical or biological ingredients thereof in the form of a liquid or solid extract. They may further be administered within conventional drug vehicles, carriers, and excipients.

The precise amounts of the kidney, extract, or derivatives thereof and the pharmaceutically-acceptable carrier, to employ in preparing the prophylactic and therapeutic compositions of the present invention are well within the skill of the art to ascertain without departing from the teachings of this disclosure. However, generally, a concentration of about 50% (by weight or volume) or higher of kidney is preferred with 100% pure kidney grind being especially preferred. For the ointment and a like, the content of renal extract is preferably a maximum that can be embodied.

In high concentrations, preparations of powder, paste, poultice, and drops are recommended in the treatment of severe infections. High concentrates such as these are preferred where tissue infection and damage is significant and where infection sites are causing considerable discomfort for the patient. These high concentrates may generally produce cure after few doses when treating skin lesions, and may have a prophylactic action of greatest duration lasting up to about few days after application. Drops for example, work well for topical or subcutaneous treatment of HPV infected lesions. As it is usually necessary to induce substantial healing of the skin as a measure against recontamination and reinfection of dermatophytes, the higher concentrates appear to be most effective as prophylaxis as well.

Preparations in the form of tea, infusion, and tincture represent a moderate concentration of renal active compounds. They may be used in place of the higher concentration often equally effective in curing viral infections. In the lower concentrations, an infusion may be used for prophylaxis or in the therapy of milder PV infections particularly when tissue damage is minimal. Infusion works well as a scalp rinse, a bath for the feet and skin, and as a douche in the treatment of vaginal infections. Infusion is also recommended particularly if patient sensitivity to the higher concentrations is causing significant discomfort. For an injection of renal compounds in deep tissue milder concentrations such as infusion are recommended for initial treatment. While injection of renal extracts have been administered safely in animal testing it is not known at this writing if data exists on treating humans with injection of renal compounds.

The precise amount of the prophylactic and therapeutic compositions to be applied to the afflicted area of the skin (such as that area where the viral-induced tumor is located) of a mammal in need thereof is well within the skill of the art to determine. However, it is desired for the quantity of the topical prophylactic and/or therapeutic compositions of the present invention to be that amount which is necessary to thinly saturate the said afflicted area. It is desired for the quantity of the subcutaneous injection to be that amount which is necessary to effectuate treatment of the said afflicted area in a reasonable course of treatment.

Recommendations for treatment given herein are general, and may be altered to suit specific conditions. If one recommended concentration for some reason appears unsuitable, the next graduation or a different one may be used. Factors to consider are the degree, type, and location of tissue infection, type and concentration of antiviral formulation, patient sensitivity to the medication, and certainly how anxious the patient is to be rid of the disorder! In most, if not all cases, daily treatment need not be continued beyond the first two weeks to completely resolve HPV infections. It will be appreciated however, that the preferred route may vary with, for example, the condition of the recipient. For each of the above-indicated utilities and indications the amounts required of the active ingredient (as above defined) will depend upon a number of factors including the severity of the condition to be treated and the identity of the recipient and will ultimately be at the discretion of the attendant physician or veterinarian.

It is said that the kidney of vertebrates and compositions thereof and especially ruminant species is comparable to that of the human body. Therefore, no problem may be caused to occur when the above penetrates into the human body through mucous membrane or wound, because the active ingredients react just as the inherently generated ingredients. Therefore, there occurs no problem or side effects from the current method of treatment. In addition, as the content of the antiviral composition is of natural source, it hardly stimulates the skin or mucous membrane. Therefore, it is quite suitable for topical or subcutaneous applications.

Never the less, it is well within the skill of the art to avert or preclude the development of skin or systemic reactions to the compositions and formulations of the present invention even though application is most likely to be topical and no such reactions have been so far experienced. Such disinfecting techniques as freezing to $-60°$ C. and using antiviral, antimicrobial, antibacterial, and/or antifungal chemical, as well as using healthy vertebrate source are sure to eliminate any such possibility.

Table 2 sets forth the major constituents of a vertebrate kidney which grossly takes into account the variations observed from batch to batch and when using different material. None of these constituents has been specifically claimed or identified in the prior art as being of therapeutic or prophylactic value in treating the viral infections of the present invention. These analyses further confirmed that no salicylic acid or other currently known agent for the treatment of viral infections such as warts is present. As set forth herein, the components of the vertebrate kidney were found effective against said viral-induced tumors and infections. The compositions of the present invention are therefore an indication of a novel and non-obvious process.

TABLE 2

Composition of samples of kidney from vertebrate.

| Compound | Compounds |
|---|---|
| 1 Threshold substances | Urea, uric acid, creatinine (from creatine phosphate), and potassium, NaCl, NaHCO$_3$, glucose, plasma, water, biomass, tissues. |
| 2 Electrolytes | Na$^+$, K$^+$, H$^+$, NH$_4^+$, Ca$^{2+}$, Mg$^{2+}$, Cl$^-$, HCO$_3^-$, HPO$_4^-$, PO$_4^{3-}$, SO$_4^{2-}$ and ions |
| 3 Acids | H$_2$CO$_3$, H$_2$PO$_4$ |
| 4 Salts | NaCl, NaHCO$_3$, Na$_2$HPO$_4$, |
| 5 Aldosterone (mineralocorticoud) | |
| 6 Antidiuretic hormone (ADH) | |
| 7 NH$_4$ Acetoacetates | |
| 8 Glutamine + aminoacids + CO$_2$ | |
| 9 Proteins and vitamins | |
| 10 Ammonia, organic acids and bases. | |
| 11 Neurotransmitters, histamine, and drugs (penicillin, atropine, morphine, and numerous others) | |

At the time of filing this patent application, the complete characterization of the active component or components responsible for the prophylactic and therapeutic effects of the kidney is not available to the inventor. However, as of the filing date of this patent application, further clinical and analytical work is diligently in progress by the inventor to refine the method of the present invention and to further characterize the active component or components. It is believed that such can be accomplished without excessive experimentation. Never the less, the active component or components of the vertebrate kidney responsible for its prophylactic or therapeutic effects in treating viral tumors, infections, and diseases are all claimed under the scope of this invention.

DESCRIPTION OF PREFERRED EMBODIMENTS

The present invention will be explained in more details with reference to the following examples which are provided to further define the invention and are in no way meant to limit the scope of the invention to the particulars of these examples.

EXAMPLES OF PHARMACEUTICAL PREPARATIONS FOR CLINICAL TRIALS

Example 1

Preparation of Liquid Extracts

A liquid suitable for topical use is prepared by mixing equal parts by weight of distilled water and ground sheep kidney in a sterilized meat grinder. The mixture is stirred thoroughly by shaking for 2 minutes in sterilized bottles to extract the kidney juices containing extra-cellular compounds into the water then allowed to settle down by the effect of gravity under refrigeration for about 24 hours. Having separated into two phases, the supernatant or clear liquid containing the active ingredients rich in activity is harvested from the solid phase containing the cell biomass which is left undisturbed. The clear liquid was then passed through a final filter (standard Bickman or Whatman filter paper) to remove cell biomass and other insolubles therefrom. The resulting composition was a renal extract useful for the treatment of viral infections that produce skin lesions such as warts. The liquid extract was distributed in aseptic flasks, frozen and further stored at −60° C. until utilization. The liquid may later be used in the form of drops using a dropper or may be incorporation into formulations of pharmaceutical medicaments or cosmetic products suitable for the purpose intended.

Example 2

Preparation of Liquid Extracts

The antiviral composition is prepared according to the method according to Example 1 wherein the final filtered liquid extract is admixed with a pharmaceutical grade ethyl alcohol to make 30% by weight alcohol solution then distributed in aseptic flasks and kept in a refrigerator without freezing.

Example 3

Formulating a Powder Preparation

The kidney of a healthy sheep is sliced into 5 millimeter thick slices then dried in a commercial dryer to a liquid-free solid using hot flow of air at 50° C. for about 24 hours. It is then finely ground to a powder form using a sterilized coffee grinder. This powder may then be mixed with distilled water to make a paste suitable for topical application to an HPV-induced lesion such as warts. Alternatively, the powder may be admixed with Vaseline or another formulation to make a lotion or a cream, or may be used as is. Application is to occur at least once daily for about four weeks to eliminate the viral-induced tumor.

Example 4

Formulating Cream Preparation

A cream, which is an oil-in-water emulsion suitable for topical application at dry conditions, was prepared by mixing at high speed 1 kg of emulsifying wax, 1 liter of glycerin, 1 liter of liquid paraffin, and 1 kg of Vaseline at 60° C. When the mixture is completely melted, six liters of liquid renal extract obtained according to the method of Example 1 was added along-with 60 grams of methyl hydroxy benzoate and 30 grams of propyl hydroxy benzoate. Mixing was continued at high speed until the mixture is completely emulsified to a cream-like consistency and was allowed to come to room temperature. This total mixture was then autoclaved and sonicated to create a sterile, homogeneous emulsion. The thus formulated cream is useful for the treatment of viral infections that produce skin lesions or warts. The quality of the obtained cream was quite desirable.

Having thus described the prophylactic and therapeutic compositions of the present invention, as well as the method for the preparation and use thereof, the following Examples are now presented for the purposes of illustration only and are neither meant to be, nor should they be, read as being restrictive. The present invention will be more readily understood by way of the specific embodiments shown in the appended examples.

Examples of Clinical Pharmacology Trials

In an ongoing vivo study of this invention which began with seven subjects involving the inventor himself and his immediate family members, infectious outbreaks have been treated with formulations comprising the composition of the present invention in different concentrations as described in the following non-limiting examples. The inventor and his immediate family members seem to be prone to HPV infections manifested by frequent and repeated outbreaks of wart legions. Some of these individuals treated to date, were previously treated with salicylic acid preparations, liquid nitrogen or electrical burning with persistent reoccurrence in all cases. Upon reappearance of the warts, the subjects enrolled into the kidney trial and have successfully completed their course of therapy. A typical usage example for the medicament is to apply a kidney or extract either pure or embodied in a carrier directly to the infected area of the skin at least once everyday for a period of two weeks. In all cases, the warts had disappeared within four weeks and recurrence of warts had not yet been detected.

Methods and Techniques

1. Panelists

At this time, a total of seven individuals have undergone the inventive therapy and all experienced the eradication of their HPV-induced tumors or lesions (warts). The panelists were males and females, ages 13 to 50, with no evidence of acute or chronic disease including dermatological problems. The test site was devoid of nevi, moles, sunburn, suntan, or scars. On numerous occasions some of the subjects have been previously treated by dermatologists with several over the counter and physician prescribed topical or subcutaneous medications to control wart progression and associated pain. Among the treatments there was liquid Nitrogen, Salicylic acid, Anaerobia, Nitric acid, and sulfuric acid that yield no noticeable improvement in the condition. Regardless of these continued treatments the wart continues to grow back causing the usual discomfort.

2. Experimental Protocol

In the first stage of this study the number and size of the tumors were compared in subjects. A further embodiment of the method of this invention comprises washing the affected area of the body with soap, rinsing the area and then placing the composition of the present invention or a formulation prepared thereof on the tumor to be treated. Topical treatments began administering the subject treatments with direct application of the antiviral medicament formulated from the composition of the present invention at least once daily for about two to four consecutive weeks. Treatments were effectuated by contacting the infected tumor sites with the particular treatment and maintaining such contact for at least ten (10) seconds to saturate the infection site, with occasional placement of medicament residue on the warts to let the treatments work-in. The warts were then observed and measured at each application.

3. Results

The results of the clinical observations hereafter discussed are summarized as follows: In all cases the surprisingly good results were the same: (1) a tingling sensation is experienced with initial application; (2) Pain and itching disappears in the first week; (3) No outbreak occurs when the composition is applied at the prodrome stage; (4) The outbreak resolves in 30 days or less when applied at the vesicular stage; (5) Longer latency periods or no further outbreaks.

The group who had received the therapeutic treatments with the composition, it was found that after about four weeks, such specimens experienced 100% fewer tumors (all subjects showed complete tumor regression and warts disappeared, thus cured). The previously infected area of skin looks perfectly normal and healed, with no trace of disease, or abnormality. This 100% reduction in tumors demonstrates the therapeutic properties of the composition of the present invention. The lack of reoccurrence of the infection on the same inflected area after treatment demonstrates the prophylactic properties of the present invention.

4. Reactions

It is noted here that with all treatments none of the subjects had developed any reactions or loss in body weight during administration of said antiviral composition. There were no symptoms or behavior changes observed as well. Apart from some occasional experience of a harmless tingling sensation during the initial course of treatment, none experienced pain, discomfort or inflammation in the infected area and there were no obvious side-effects observed. All the subjects successfully passed a soon-after blood test showing no sign of infection what so ever.

5. Conclusion

In summary then, this study demonstrates both the prophylactic and therapeutic properties of the compositions of the present invention for the prevention and/or treatment of viral-induced tumors, lesions and diseases in humans as well as other mammals. It is concluded that the composition of the present invention exhibited a therapeutic and prophylactic effect on warts. Therefore, this result suggests that the kidney, it extracts, or compositions thereof are useful in the treatment of viral-induced infections and tumors such as warts.

The following examples are provided to further define the invention without, however, limiting the invention to the particulars of these examples.

Example 5

Use of Sheep Kidney to Treat Cutaneous Warts

Case: The inventor of the present invention, who is a 37 years old healthy middle-eastern male, suffered for the first time from a human papillomavirus (HPV) infection manifested in the form of an outbreak of plurality (about 10) of benign cutaneous warts on the back of his right hand over a period of few months. The warts were rounded with a base diameter ranging from 3 to 5 mm, and a height at the peak ranging from 3 to 5 mm (note: the size of the wart is immaterial under this method) with the larger ones having white flakey dry pinnacle. There was no pain or discomfort associated with the warts, however, they were embarrassingly unsightly and appeared to increase with time both in size and number, so no doubt he wanted them removed. Having seen several of his immediate family members with the same type of infection underwent numerous painful electrocauterization treatments with frequent persistence and reoccurrence of the warts he decided to seek another alternative.

Treatment: The inventor obtained a commercially available sheep kidney, cut it into small cubes ranging in size from 1 to 2 inches, and rubbed one of them repeatedly on the wart lesions over a period of time (about 20 to 30 seconds) to saturate the tumor and allow a residue of the kidney juice to remain on surrounding tissue. The infected area was wrapped with a clean cotton cloth to allow the dose to be absorbed into the skin over night and avoid contaminating the bed sheets and covers. The infected area was then washed with the patients regular hand soap bar in the morning. The procedure was repeated every night for the next two weeks using one of the remaining kidney cubes which was kept frozen and thawed to room temperature before use. By then the kidney cubes were all consumed and there was not observed any significant change in the size or number of wart lesions with the naked eye.

Results: Surprisingly after the third week from the beginning of the course of treatment a conspicuous effect was observed; the warts appeared smaller in both size and number with the larger ones seemingly rejuvenated (i.e. the warts seemed smaller and younger with the white flakey dry pinnacles disappeared). After the fourth week all of the warts have completely disappeared with no trace what so ever leaving behind a smooth healthy skin free from any signs of a previous infection. The patient reportedly experienced only an occasional tingling sensation but no side effects either during or after the course of treatment. The subject showed no sign of blood infection in a soon-after blood test and the warts have not recurred on the same hand ever since.

The inventor was very pleased with the rapid and conclusive elimination of the warts and is convinced that the sheep kidney contains inhibiting compound(s) that are highly effective antiviral cytostatic, cytotoxic, antimitotic agent(s).

Example 6

Use of Sheep Kidney Liquid Extract as a Topical Therapeutic Agent

Case: The inventor of the present invention and his immediate family members have constantly experienced frequent wart outbreaks resulting from exposure to HPV virus, which causes warts in humans. A brother of inventor who is 33 years old male has had numerous occurrences of warts over the last 20 years for which all available methods of treatment have been used including numerous painful electrocauterization treatments, excision using liquid nitrogen, and using various salicylic acid preparations by a dermatologist. With these conventional treatments the warts subsided, however they only returned after a period of time and were a constant source of aggravation. By the time of treatment the infected area had developed a total of 20 warts, ranging in diameter and height from 2 to 5 mm, and had a semi-spherical shape. Some of the larger warts had developed raised white dry spots on the surface. Moreover, the subject has developed a couple of larger warts on his hands about 7 mm in diameter and, typically, the warts became secondarily infected and were very painful.

Treatment: A controlled study of the therapeutic effects of the crude cell-free renal extract obtained as described above in Example 2 was performed. The course of treatment began with daily applications to the site of the infection (warts) the sheep kidney liquid extract at bedtime then wrapping with bandages to avoid soiling the bed and cloths. The composition was applied topically with cotton gauze in an amount enough to saturate the tumor area and surrounding tissues. A small amount of residue was allowed to remain on the affected area and surrounding tissue over night then washed with a regular hand soap bar in the morning.

Results: After two consecutive weeks of treatment the pain of the tumor had decreased and the warts were beginning to shrink in size. This lack of discomfort caused the subject to forget about the wart, and he had not looked at it since treatment. No irritation or redness resulted from leaving the residue and the tumor continued to decrease in size, even though it was ceased the application of medicament after the initial two weeks. The tumors were noticeably smaller and finally had reduced to small dots by the third week. After four weeks of such usage the warts had totally disappeared with no further outbreaks or incidents of reoccurrence experienced ever since leaving behind a healthy skin devoid of any visible marks or signs of a previous infection what so ever.

Example 7

Use of Dry Sheep Kidney Powder as a Topical Therapeutic Agent

Case: The inventor of the present invention described in Example 5, was afflicted with a single benign cutaneous wart on the back of his left hand close to the index finger about 1 mm in diameter. The wart was hardly noticeable but grew over a period of few months to 2 mm and appeared to increase in size with time. Having tried the composition of the present invention successfully to treat the warts outbreak on right hand in Example 5, he decided to use the same on the left hand as well.

Treatment: A controlled study of the therapeutic effects of a powder formulation obtained from the composition of the present invention as described above in Example 3 was performed. The powder was mixed with distilled water to make an antiviral preparation with a paste-like consistency suitable for topical application to the HPV-induced lesion (wart). The course of treatment began with daily applications to the site of the infection (warts) the sheep kidney in the form of paste each evening prior to retiring to bed then wrapping with bandages to avoid soiling the bed and cloths. For the next two weeks the composition was applied topically with cotton gauze in an amount enough to saturate the tumor area and surrounding tissues. A small amount of residue was allowed to remain on the affected area and surrounding tissue over night then washed with regular hand soap bar in the morning.

Results: After two weeks it was determined that no inflammatory reaction or toxic effect was observed. After four weeks of initial treatment the wart had totally disappeared (completely healed) without damage to the skin in the target area and no side effect or trace what so ever leaving behind a healthy skin. Upon final inspection, the skin appeared normal as if it had not been previously infected and no new tumors were evident by the time of this filing.

Example 8

Use of Sheep Kidney Cream Formulation as a Topical Therapeutic Agent

Case: The mother of the inventor who is 60 years old home maker had endured an outbreak of human papillomavirus infected tumors (warts) over the last 3 years all over the back of her hands and fingers. At the initial examination, the warts were very large, pigmented and painful. The skin around the warts was very dry with heavy callous formations. By the time of treatment the infected area had developed almost innumerable warts ranging in diameter and height from 2 to 5 mm and had a semi-spherical shape. Moreover, the subject has developed a single small wart about 2 mm in diameter just a quarter of an inch above the left side of her upper lips. The patient experienced pain and embarrassment due to the numerous warts.

Treatment: A controlled study of the therapeutic effects of a cream formulation obtained from the composition of the present invention as described above in Example 4 was performed. The course of treatment began with daily applications to the site of the infection (warts) the cream formulation at bedtime then wrapping with bandages to avoid soiling the bed and cloths. The wart about the face was covered with small dressing supported by an adhesive tape. The composition was applied topically in an amount enough to saturate the tumor area and surrounding tissues and rubbed into each of the several warts for ten seconds utilizing three fingers. The applied cream was allowed to remain on the affected area and surrounding tissue over night to be absorbed into the skin then washed with the subjects regular hand soap bar in the morning. This treatment was repeated for the following two weeks during which the subject reported experiencing an occasional subcutaneous tingling sensation in the tumors.

Results: Quite unexpectedly, the pain of the tumor had decreased and the warts were beginning to shrink in size after two weeks of treatment with no irritation or redness resulted. It was observed that at first the surface layers of the wart began to exfoliate exposing large erythematous papules. Then interestingly, the warts did not just diminish in size by flaking or peeling, they became gradually smaller in size (by approximately 0.3 mm per day) and after four weeks of initial treatment they had totally disappeared with no further outbreaks or incidents of reoccurrence experienced ever since leaving behind a healthy skin devoid of sequela, scarring or visible marks of a previous infection what so ever.

Example 9

Use of Sheep Kidney as a Topical Therapeutic Agent in Other Animals

A horse with wart-type tumors on its nose was treated for a two week period. Treatments were conducted by dabbing small pieces of the sheep kidney, prepared according to the method of Example 5, onto the warts on the horse's noses. This was repeated twice during each treatment, so that the afflicted area and surrounding skin were soaked. By approximately 21 days post-initiation of treatments the warts began changing in appearance (they appeared smaller). By day 30, it was noted that the warts had completely disappeared, thus healed.

These results demonstrate that the sheep kidney contains active component(s) which is absorbed in the HPV infected cells and slows down tumoral progression. This inhibition might be a direct effect on the tumor cells or an anti-angiogenesis mediated effect interfering with tumor growth. They also suggest that the kidney extracts as well contain inhibitory activity since their administration caused inhibition of tumoral cell proliferation suggesting they may contain active components possessing inhibitory activity. Furthermore, the antiviral formulations from the compositions of the present invention which comprises kidney or its extracts in the form of, for example, cream, powder, paste, and liquid drops were equipotent in their ability to inhibit tumoral cell proliferation which suggests that the inhibition factor(s) are not denatured by the procedure of preparation disclosed herein.

The mechanism by which these antiviral compositions work is still not known but it is believed that the mode of action of the compositions of the present invention may be directly antiviral or anti-tumor in nature. The inventor believes that the sheep kidney contains inhibiting compound(s) that are highly effective antiviral agent(s) with cytostatic, cytotoxic and antimitotic course of action which function to neutralize the virus that creates the wart. One way of such action is through inhibition of viral replication. It is also possible that the mode of action of the compositions disclosed herein may be the result of a general stimulation of the immune system.

If desired, the prophylactic and therapeutic compositions may be applied before infection in a prophylactic treatment to prevent initial infection. We have found that the prophylactic and/or therapeutic compositions have significant tumor reducing potential when applied either shortly after infection, or when applied to existing tumors. It is contemplated that such applications will be performed at least one time per day as long as the tumors persist. However, the precise frequency of these applications may be increased and/or decreased as desired or needed, as is well within the skill of the art to determine.

Since warts are caused by human papillomavirus (HPV) of different types and the antiviral composition of the present invention disclosed herein can eradicate this virus, it is contemplated that this composition may be useful in methods of eradicating other papillomaviruses (PV) such as cottontail rabbit papilloma virus (CRPV), equine papillomavirus (EPV) and Bovine papillomavirus (BPV). It may also have effectiveness against Papovavirus (PPV) for which Papillomavirus are subspecies, as well as other DNA and RNA viruses. Its effect on other DNA and RNA viruses needs further investigation. The fact that the prophylactic and therapeutic composition disclosed herein appears to be extremely effective in eradicating common warts indicates its possible effectiveness against other viral-induced infections, tumors and diseases as well. The compositions and methods of the present invention also contemplate utility in the treatment of other human and mammalian papillumavirus infections such as genital and laryngeal papilloma which are a genuine nuisance and are very hard to eradicate.

It is quite evident from the clinical experience to date, that the sheep kidney which is a main component of the present invention has been outstandingly effective in the treatment, prevention and elimination of warts. The complete eradication of the warts with no recurrence is truly a surprising result as the medical community still searches for a cost effective and efficacious method to control this human malady. In light of these results, the inventor has concluded that kidney or components thereof and in particular that of sheep is not only an antiviral agent against HPV and perhaps other viruses but it may also be a chemoprotective agent effective for treatment of cancerous or precancerous lesions of the skin, respiratory and the genital tract.

While the sheep kidney has shown outstanding therapeutic and prophylactic potentials in the prevention and treatment of viral-induced infections and tumors such as warts, it is contemplated that any other source of kidney is effective in the present invention. Kidney from other vertebrates, which have many therapeutic properties in common with sheep, may be used in place of sheep kidney described herein.

At this time, application of the present invention has been limited to topical application. However, continued clinical study and testing is in progress to determine the therapeutic effect of subcutaneous administration of the composition of the present invention in vivo.

As to the therapeutic properties of renal compounds and are several actions I believe to be at work in the operation of the medication of the current invention. While some of the actions described herein are factual, others are theoretical, or hypothetical, and are set forth as possibilities, and are not intended to be binding. They represent an attempt to further explain the operation of the current invention, and to give direction to areas warranting further research.

INDUSTRIAL APPLICABILITY

Viral-induced tumors, especially of the skin, are very common. These tumors are typically very difficult to treat, control and prevent. The medical community has searched for decades for new therapies to treat this common human malady. The present invention provides a simple, safe, reliable, and cost-effective method to treat and prevent these viral-induced tumors.

COMPARISON WITH PRIOR ART PRODUCTS

Since we are not the first to find a great interest in the treatment of HPV tumors, we have verified the unique character of the antiviral composition prepared by the present process in side-by-side comparison tests with other products described or deducible from the prior art. The above results show that the present invention provides a product of unexpectedly good antiviral and antitumoral activity that is both cheaper and easier to prepare and apply with no undesirable side effects. The numerous advantages of the present invention are disclosed herein with more details.

CONCLUSIONS

From the studies disclosed herein, the vertebrate kidney and especially that of sheep demonstrated effectiveness in the treatment of viral skin infections and specific antiviral properties against HPV infections. The method according to this invention includes administering raw kidney or derivatives thereof to an area of a mammal which is anticipated to evidence viral-induced tumor growth, or an area which presently exhibits viral-induced tumor growth (i.e., warts) to prevent or eliminate the tumor.

The process of the present invention has been demonstrated as one that provides for the production of an effective antiviral composition of a great clinical value. The antiviral composition produced according to the method of this invention comprises a multiplicity of activities that are recovered in good yields. The above illustration in addition to demonstrating the therapeutic activity of renal compounds also suggests the possibility of antimicrobial inhibiting activity which is responsible for such dramatic healing results. Since the cases treatment, neither the wart has returned nor have new ones arisen. It has been determined through clinical evaluation that once the method of this invention is initiated, no matter what size, the warts begin to shrink and will totally disappear after a period four weeks or less of treatment.

The method of the present invention provides an effective therapeutic and/or prophylactic antiviral composition which is not dependent upon the patient's immune system or health status. Furthermore, because of the natural source of the antiviral composition, the compositions of the present invention can be used quite safely as compared with those in the prior art because side effects, such as scarring and stimulation to the skin, are avoided. Accordingly, the composition of the present invention is advantageously used as raw material for the therapeutic or prophylactic treatment of viral-induced infections, tumors, and diseases or to prepare cosmetic, medical or pharmaceutical products for treating the same.

DEFINITIONS

As used herein and in the claims, the term "prophylactic or therapeutic" treatment refers to administration to the host of the papillomavirus medicament. If it is administered prior to exposure to the virus, the treatment is prophylactic (i.e., it protects the host against infection), whereas if administered after infection or initiation of the disease, the treatment is therapeutic (i.e., it combats the existing infection).

As used herein and in the claims, the term "compounds of the present invention" refers to at least one of the following; the kidney itself or portions or extracts thereof, and any active compounds, as well as derivatives, metabolites and precursors of such compounds, and pharmaceutically acceptable salts, analogs, or conjugates of any of these compounds either alone or in a cosmetic or pharmaceutical preparation or a medicament, or admixture in a substantially uniform pharmacologically-acceptable excipient or an adjuvant.

As used herein and in the claims, the term "renal compounds" is meant to include at least one of the following; the kidney itself or portions or extracts thereof, and any active component or components that are isolated therefrom, as well as derivatives, metabolites and precursors, salts, analogs, or conjugates of any of these compounds.

As used herein and in the claims, the term "renal extracts" shall mean: (1) the actual liquid and solid extracts derived from the kidney and/or (2) the active ingredients, components, compositions, or constituents, isolates, or derivatives from the kidney.

By the terms "derivatives of" and "derived from" when used in reference to the kidney or extracts, what is meant are compositions or components, such as particular enzymes or combinations of enzymes, which have either been obtained (derived or isolated) from the kidney or extracts. By way of illustration, an example of such a derivative would be a renal extract which has been concentrated or filtered. The terms "derivatives of" and "derived from" are used equally to refer to compositions and compounds which are both identical to those compositions or components of the kidney or extract and which demonstrate the same prophylactic and therapeutic properties of the kidney or extracts. By way of illustration, such definition includes components of the kidney or extract itself (such as the active agent thereof) which have been isolated (and, if desired, purified) from the kidney or its extract. By way of further illustration, such definition also includes compositions or compounds which have been constructed (i.e., synthetically constructed) to mimic the active agent(s) having the prophylactic and therapeutic properties of the kidney or extracts of the present invention.

As used herein and in the claims, the term "papillomavirus disease" refers to any kind of disease or infection caused by the virus, including benign and malignant tumors such as cancers and warts.

As used herein and in the claims, the term "viral disease" refers to an abnormal state or condition characterized by viral transformation of cells, viral replication, and proliferation, such as the lack of independent metabolism, the ability to replicate only within living host cells, the ability to reproduce with genetic continuity, and the possibility of mutation. Such viral diseases or infections include but are not limited to: DNA viruses such as papovavirus, papillomavirus, and human papillomavirus induced tumors or wart.

As used herein and in the claims, "Treating viral disease" refers to slowing, interrupting, arresting, or stopping the viral transformation of cells or the replication and proliferation of the virus, and does not necessarily indicate total elimination of the virus.

By the term "effective amount" what is meant is an amount which is effective for either prophylactic or therapeutic purposes to prevent or mitigate the growth of new or existing viral-induced tumor(s) in question.

EQUIVALENTS

This invention has been described hereinabove, although with reference to a plurality of illustrative exemplary and preferred embodiments, it is to be understood that is in no way to be construed as limiting. However, it is readily appreciated that, from reading this disclosure, the invention may be embodied in other specific forms without departing from the spirit or essential characteristics or attributes to bring modifications by replacing some elements of this invention as practiced by their equivalents, which would achieve the same goal thereof and accordingly reference should be made to the appended claims, rather than to the foregoing specification, as indicating the scope of the invention. Accordingly, those skilled in the art will recognize, or be able to ascertain using no more than routine experimentation, many equivalents to the specific embodiments and the scope of the invention being indicated by the appended claims described herein. Such equivalents, obvious variations, and all changes which come within the meaning and equivalency of the claims are therefore intended to be encompassed therein and are deemed covered by the claims of this invention.

What I claim as my invention is:

1. A topical pharmaceutical composition comprising:
   vertebrate kidney or a concentrate thereof;
   an emulsifier or dispersing compound; and
   a carrier suitable for topical application, which is oil-, or organic-based;
   wherein said vertebrate kidney or concentrate thereof is present in said composition in an amount of at least 50% by weight or volume and said vertebrate is a ruminant; and wherein said carrier is petroleum jelly.

2. The composition of claim 1, which further comprises a topical or subcutaneous anesthetic.

3. A topical pharmaceutical composition comprising:
   vertebrate kidney or a concentrate thereof;
   an emulsifier or dispersing compound; and
   a carrier suitable for topical application, which is oil-, or organic-based;
   wherein said vertebrate kidney or concentrate thereof is present in said composition in an amount of at least 50% by weight or volume and said vertebrate is a ruminant; and wherein said carrier comprises emulsifying wax, glycerin, liquid paraffin and petroleum jelly.

4. The composition of claim 1, wherein said vertebrate kidney is prepared for the composition by a process, which comprises the steps of:
   grinding the kidney;
   homogenizing the ground kidney with solvent;
   separating soluble renal extract from solid particles of renal cell mass; and
   isolating the renal extract from the solvent.

5. The composition of claim 1, wherein said concentrate is prepared for the composition by a process comprising the steps of:
   grinding the kidney;
   homogenizing the ground kidney with solvent;
   separating soluble renal extract from solid particles of renal cell mass; and
   concentrating the soluble renal extract.

6. A dry powder pharmaceutical composition, comprising:
   powdered vertebrate kidney or a powdered concentrate thereof; and
   a powdered talc carrier;
   wherein said powdered kidney or concentrate thereof is present in said composition in an amount of at least 50% by weight and volume, and wherein the vertebrate is a ruminant.

* * * * *